(12) United States Patent
Nakao et al.

(10) Patent No.: US 8,609,022 B2
(45) Date of Patent: Dec. 17, 2013

(54) MEDICAL HEAT EXCHANGER, MANUFACTURING METHOD THEREOF AND ARTIFICIAL LUNG DEVICE

(75) Inventors: Shota Nakao, Osaka (JP); Tomokazu Niitsuma, Hiroshima (JP); Hideki Izumida, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 429 days.

(21) Appl. No.: 12/864,356

(22) PCT Filed: Jan. 22, 2009

(86) PCT No.: PCT/JP2009/050981
§ 371 (c)(1),
(2), (4) Date: Jul. 23, 2010

(87) PCT Pub. No.: WO2009/093659
PCT Pub. Date: Jul. 30, 2009

(65) Prior Publication Data
US 2010/0290947 A1    Nov. 18, 2010

(30) Foreign Application Priority Data

| Jan. 23, 2008 | (JP) | 2008-012869 |
| Mar. 21, 2008 | (JP) | 2008-074172 |
| Apr. 24, 2008 | (JP) | 2008-114224 |
| Jun. 17, 2008 | (JP) | 2008-158151 |

(51) Int. Cl.
*A61M 1/00*    (2006.01)
*A61M 37/00*    (2006.01)

(52) U.S. Cl.
USPC .......................... 422/46; 604/6.14; 604/6.13

(58) Field of Classification Search
USPC ............... 422/44–48; 607/113; 165/157, 175; 29/890.05; 604/4.01, 5.01, 7, 19, 23, 604/317
See application file for complete search history.

(56) References Cited

U.S. PATENT DOCUMENTS

| 4,065,264 | A | * | 12/1977 | Lewin | 422/46 |
| 5,225,161 | A | * | 7/1993 | Mathewson et al. | 422/46 |
| 5,294,397 | A | * | 3/1994 | Oshiyama et al. | 264/251 |
| 6,117,390 | A | * | 9/2000 | Corey, Jr. | 422/45 |

(Continued)

FOREIGN PATENT DOCUMENTS

| EP | 1715279 A1 * | 10/2006 |
| JP | 5-157468 | 6/1993 |

(Continued)

*Primary Examiner* — Philip R Wiest
*Assistant Examiner* — Benjamin Klein
(74) *Attorney, Agent, or Firm* — Hamre, Schumann, Mueller & Larson, P.C.

(57) ABSTRACT

A medical heat exchanger includes a thin tube bundle 2 in which a plurality of heat transfer thin tubes 1 for letting heat medium liquid flow therethrough are arranged and stacked, seal members 3a to 3c sealing the thin tube bundle while allowing both ends of the heat transfer thin tubes to be exposed and forming a blood channel 5 which allows blood to flow therethrough so that the blood comes into contact with each outer surface of the heat transfer thin tubes; a housing 4 containing the seal members and the thin tube bundle and provided with an inlet port 8 and an outlet port 9 of the blood positioned respectively at both ends of the blood channel; and a pair of heat transfer thin tube headers 6, 7 forming flow chambers 14a, 14b, 15a, 15b that respectively surround both ends of the thin tube bundle and having an inlet port 6a and an outlet port 7a of the heat medium liquid. The thin tube bundle is divided into a plurality of thin tube bundle units 12a to 12c, and the heat transfer thin tube headers are configured so that the heat medium liquid passes through the plurality of the thin tube bundle units successively. Heat exchange efficiency is enhanced while the flow speed of the heat medium liquid flowing through the heat transfer thin tubes is increased to suppress the increase in volume of the blood channel.

19 Claims, 24 Drawing Sheets

(56) References Cited

U.S. PATENT DOCUMENTS

| | | | | |
|---|---|---|---|---|
| 6,131,644 | A | * | 10/2000 | Kohara et al. .................... 165/10 |
| 2007/0137843 | A1 | * | 6/2007 | Gievers ........................ 165/166 |
| 2008/0031773 | A1 | * | 2/2008 | Eccleston ....................... 422/44 |
| 2009/0018629 | A1 | | 1/2009 | Yoshida et al. |

FOREIGN PATENT DOCUMENTS

| | | |
|---|---|---|
| JP | 2001-50685 | 2/2001 |
| JP | 2003-28539 | 1/2003 |
| JP | 2005-224301 | 8/2005 |
| WO | WO 2007077816 A1 * | 7/2007 |

* cited by examiner

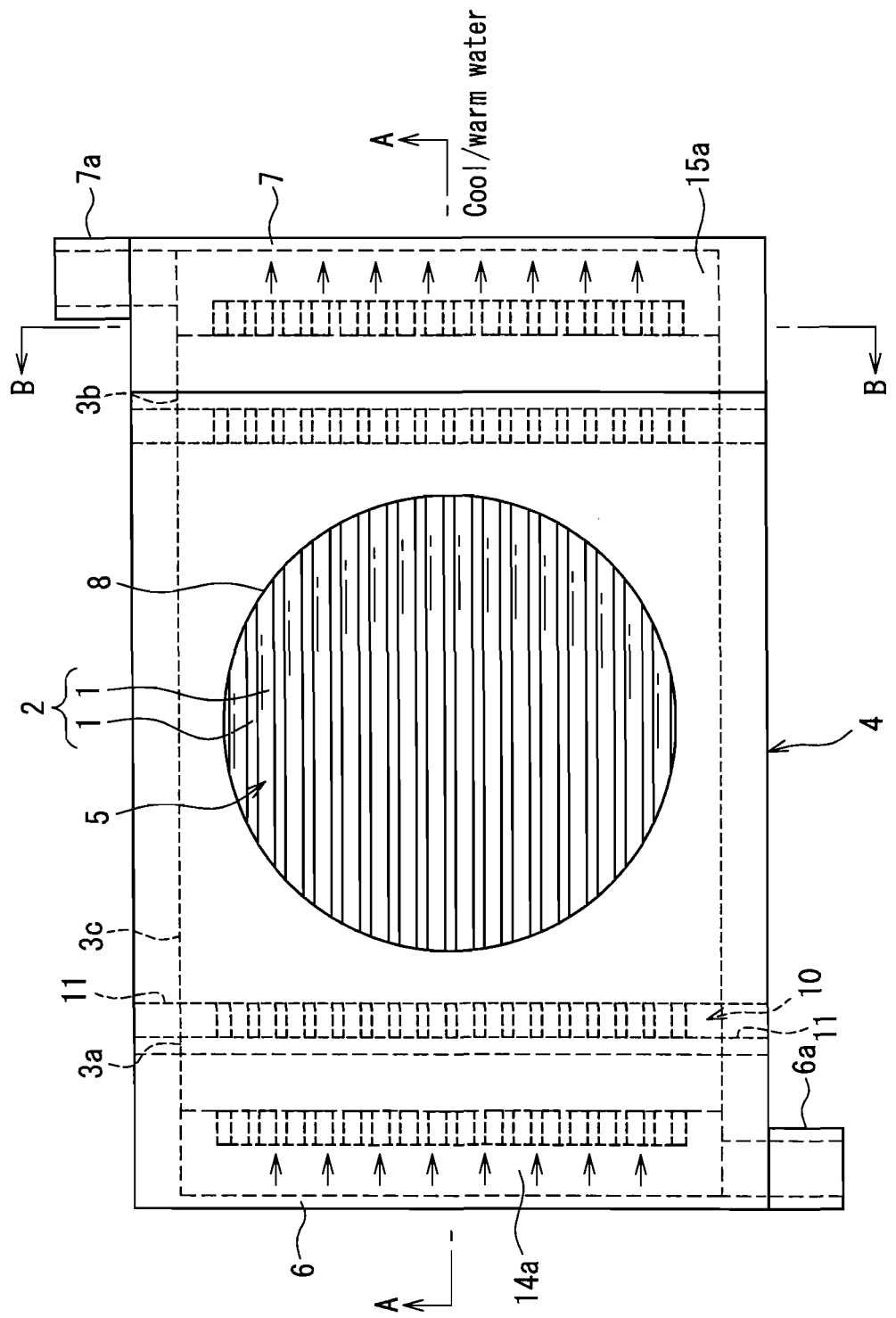

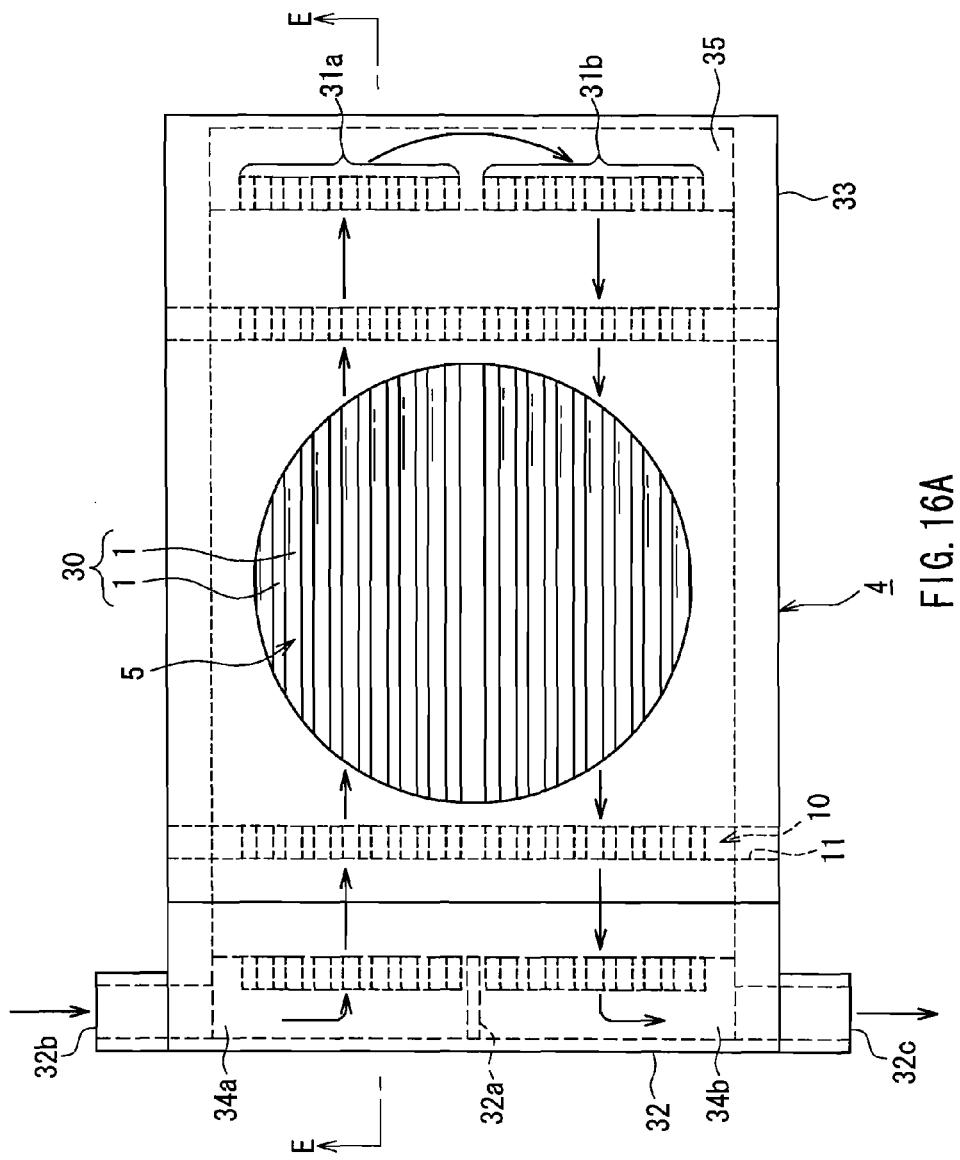

MEDICAL HEAT EXCHANGER, MANUFACTURING METHOD THEREOF AND ARTIFICIAL LUNG DEVICE

TECHNICAL FIELD

The present invention relates to a heat exchanger, in particular, to a medical heat exchanger suitable for use in medical equipment such as an artificial lung device, a method for producing the heat exchanger, and an artificial lung device having the heat exchanger.

BACKGROUND ART

In heart surgery, a cardiopulmonary bypass device is used when causing the heartbeat of a patient to cease and taking the place of the heart to perform the respiration and circulation functions during the cessation of the heartbeat. Further, during the surgery, in order to reduce the amount of oxygen to be consumed by the patient, it is necessary to lower the body temperature of the patient and maintain the lowered temperature. Therefore, the cardiopulmonary bypass device is provided with a heat exchanger for controlling the temperature of blood collected from the patient.

As such a medical heat exchanger, conventionally, a bellows tube type heat exchanger and a multitubular heat exchanger (see, for example, Patent Document 1) are known. Of them, the multitubular heat exchanger has an advantage of a higher heat exchange efficiency compared with that of the bellows tube type heat exchanger, because the multitubular heat exchanger can obtain a larger heat exchange area, assuming that the volume of the multitubular heat exchanger is the same as that of the bellows tube type heat exchanger.

A conventional exemplary multitubular heat exchanger will be described with reference to FIGS. 20A-20C. FIG. 20A is a top view of a multitubular heat exchanger, and FIG. 20B is a side view thereof. FIG. 20C is a perspective view illustrating an inside of a housing of the heat exchanger, which is illustrated partially in a cross-section.

The heat exchanger includes a thin tube bundle 102 composed of a plurality of heat transfer thin tubes 101 allowing cool/warm water that is heat medium liquid to flow, seal members 103a-103c sealing the thin tube bundle 102, and a housing 104 containing these components.

A plurality of the heat transfer thin tubes 101 are arranged in parallel and stacked to form the thin tube bundle 102. As illustrated in FIGS. 20A and 20C, the seal member 103c at the center is provided with a blood channel 105 having a circular cross-section at the center in a longitudinal direction of the thin tube bundle 102. The blood channel 105 functions as a heat exchange channel for distributing blood that is liquid to be subjected to heat exchange so that the blood comes into contact with each outer surface of the heat transfer thin tubes 101. The seal members 103a, 103b at both ends respectively expose both ends of the thin tube bundle 102.

As illustrated in FIG. 20B, the housing 104 has a blood inlet port 106 for introducing blood into the housing 104 and a blood outlet port 107 for discharging the blood out of the housing 104, which are placed at upper and lower ends of the blood channel 105. Further, gaps 108 are provided between the seal members 103a-103c respectively. The housing 104 is provided with leaked liquid discharge holes 109 corresponding to the gaps 108.

In the above-mentioned configuration, blood is allowed to flow in from the blood inlet port 106 and flow out of the blood outlet port 107 after passing through the blood channel 105. Simultaneously, as illustrated in FIGS. 20A and 20B, cool/warm water is allowed to flow in from one exposed end of the thin tube bundle 102 and flow out of the other exposed end thereof. Thus, the heat exchange is performed between the blood and the cool/warm water in the blood channel 105.

The gaps 108 are provided for the purpose of detecting leakage when the blood or cool/warm water leaks due to seal leakage. More specifically, when leakage from the third seal member 103c occurs, the leaked blood appears in the gaps 108 and thus, the leakage can be detected. Further, even when the cool/warm water leaks due to the leakage from the first seal member 103a or the second seal member 103b, the leaked cool/warm water appears in the gaps 108, and thus, the leakage can be detected. The blood or cool/warm water having leaked in the gaps 108 is discharged outside of the heat exchanger from the leaked liquid discharge holes 109.

Patent Document 1: JP 2005-224301 A

DISCLOSURE OF INVENTION

Problem to be Solved by the Invention

There is a demand for the heat exchange efficiency of the above-mentioned multitubular heat exchanger to be enhanced further. This is because it is necessary to enhance the heat exchange efficiency in order to minimize the priming volume of blood in the blood channel 105 and further obtain sufficient heat exchange ability.

In the case of a heat exchanger for an artificial lung considered by the inventors of the present invention, it was found that the heat exchange efficiency desirably is 0.43 or more from a workable standpoint. The heat exchange area required for achieving the target value was 0.014 m$^2$ at a blood flow rate of 2 L/min. If this is applied to a configuration in which the ability of the heat exchanger is enhanced to a blood flow rate of 7 L/min., as a result of heat exchange area simulation, it was found that a heat exchange area of 0.049 m$^2$ is required for obtaining a heat exchange efficiency of 0.43 or more. Herein, the heat exchange efficiency is defined by the following expression.

$$\text{Heat exchange efficiency} = (T_{BOUT} - T_{BIN})/(T_{WIN} - T_{BIN})$$

$T_{BIN}$: blood inflow side temperature
$T_{BOUT}$: blood outflow side temperature
$T_{WIN}$: heat medium (water) inflow side temperature For example, the following is found: when using the heat transfer thin tubes 101 with an outer diameter of 1.25 mm, if the stacking number (number of thin tube layers) of the heat transfer thin tubes 101 is set at six, a heat exchange area of 0.057 m$^2$ can be obtained. However, when heat exchange efficiency was measured with an opening diameter of the blood channel 105 set at 70 mm, using a heat exchange module including the thin tube bundle 102 with such a six-layered configuration, only a value much lower than the target value (i.e., 0.24) was obtained.

Then, a heat exchange module was produced in which the heat transfer thin tubes 101 with an outer diameter of 1.25 mm were used, an opening diameter of the blood channel 105 was set at 70 mm, and the number of thin tube layers was increased variously, and heat exchange efficiency was measured using the module. As a result, it was found that, in order to achieve a heat exchange efficiency of 0.43, it is necessary to set the number of thin tube layers at 18 or more. However, if the number of thin tube layers is set at 18 under the above-mentioned conditions, the blood priming volume in the blood channel becomes 42.3 mL. This exceeds 30 mL, which is a desired value of the blood priming volume. In order to set the blood priming volume at 30 mL or less, the number of thin tube layers should be set at 13 or less according to a calculation.

Thus, it is difficult to obtain the desired heat exchange efficiency merely by increasing a heat exchange area. Therefore, the cause that seems to decrease heat exchange efficiency was analyzed. Consequently, as the cause for decreasing heat exchange efficiency, it was found that a flow speed of cool/warm water flowing through lumens of the heat transfer thin tubes 101 has large influence. This is considered to be caused by the influence of a flow speed of cool/warm water on a change in a film resistance.

An object of the present invention is to provide a medical heat exchanger capable of enhancing heat exchange efficiency while controlling the flow of heat medium liquid in lumens of heat transfer thin tubes appropriately, thereby reducing the volume of a heat exchange region.

Means for Solving Problem

A medical heat exchanger of the present invention includes: a thin tube bundle in which a plurality of heat transfer thin tubes for letting heat medium liquid flow through a lumen are arranged and stacked; a seal member sealing the thin tube bundle while allowing both ends of the heat transfer thin tubes to be exposed and forming a blood channel that allows blood to flow therethrough so that the blood comes into contact with each outer surface of the heat transfer thin tubes; a housing containing the seal member and the thin tube bundle and provided with an inlet port and an outlet port of the blood positioned respectively at both ends of the blood channel; and a pair of heat transfer thin tube headers forming flow chambers that respectively surround both ends of the thin tube bundle and having an inlet port and an outlet port of the heat medium liquid.

In order to solve the above-mentioned problem, the thin tube bundle is divided into a plurality of thin tube bundle units each including a plurality of the heat transfer thin tubes, and the heat transfer thin tube headers are configured so that the heat medium liquid to be introduced passes through the plurality of thin tube bundle units successively.

Effects of the Invention

According to the above-mentioned configuration of the medical heat exchanger of the present invention, heat medium liquid successively passes through a plurality of groups of thin tube bundle units into which the thin tube bundle is divided, and hence, the flow speed of cool/warm water flowing through the heat transfer thin tubes of each thin tube bundle unit can be increased. Consequently, the heat exchange efficiency can be enhanced while the film resistance in the inner walls of the heat transfer thin tubes is reduced to suppress the increase in volume of a heat exchange region.

BRIEF DESCRIPTION OF DRAWINGS

FIG. 1A is a top view illustrating a configuration of a medical heat exchanger in Embodiment 1

FIG. 16A is a top view illustrating a configuration of a medical heat exchanger in Embodiment 6.

Figure 1B:
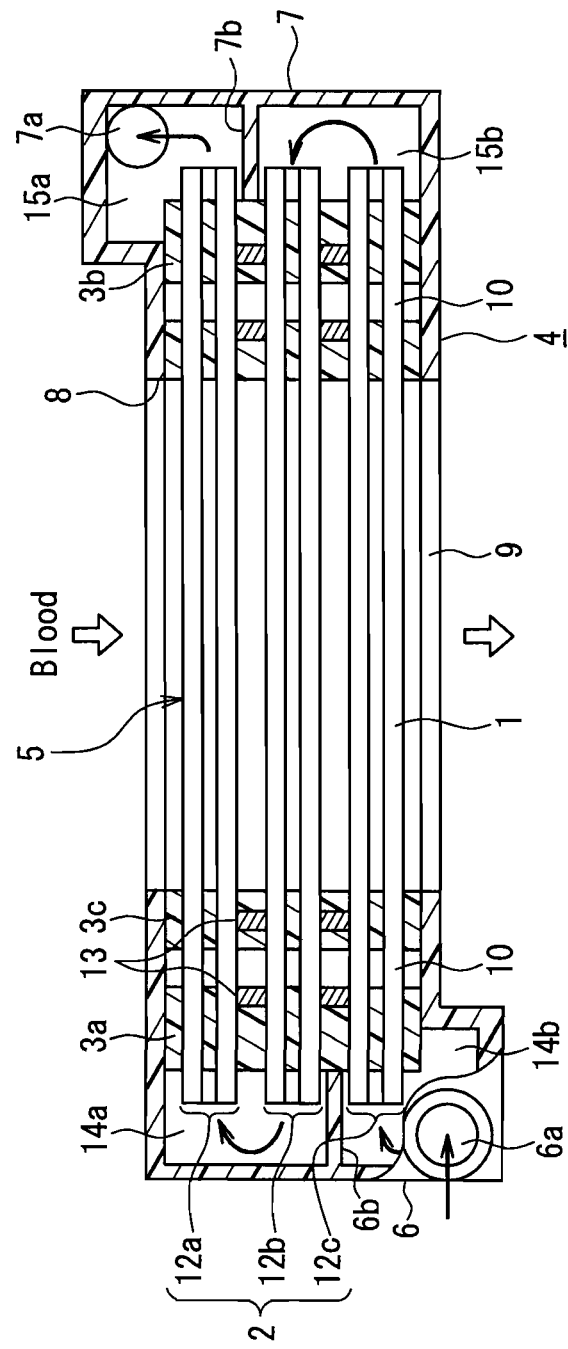
FIG. 1B is a cross-sectional view taken along the line A-A of the medical heat exchanger.

DESCRIPTION OF THE INVENTION 1, 101 heat transfer thin tube
2, 30, 36, 102 thin tube bundle
3a-3c, 103a-103c seal member
4, 104 housing
5, 105 blood channel
6 cool/warm water inlet header
6a, 32b, 38c cool/warm water inlet port
6b, 7b, 32a, 38a, 38b partition wall
7 cool/warm water outlet header
7a, 32c, 38d, 38e cool/warm water outlet port
8, 106 blood inlet port
9, 107 blood outlet port
10, 108 gap
11, 109 leaked liquid discharge hole
12a-12c first to third thin tube bundle unit
13 spacer
13a, 13b insertion portion
13c connecting portion
14a, 15a upper flow compartment
14b, 15b lower flow compartment
16a-16d thin tube row holding member
17 thin tube receiving concave portion
18 interval
19 coupling frame
20, 20a, 20b insertion member
21 annular rib
22 connection rib
23 annular frame
24 clearance
25 connecting portion
25a connecting protrusion
26 frame
26a positioning rib
27 positioning protrusion
28 bridge member
29 fitting portion
31a, 31b thin tube bundle unit
32, 38 cool/warm water inlet/outlet header
33, 39 cool/warm water reflux header
34a, 40b inlet chamber
34b, 40b, 40c outlet chamber
35, 41 reflux chamber
37a center thin tube bundle unit
37b, 37c side thin tube bundle unit
50 heat exchanger
51 artificial lung
52 housing
53 gas inlet path
54 gas outlet path
55 hollow fiber membrane
56 seal member
57 blood channel
58 blood outlet port

DESCRIPTION OF THE INVENTION

A medical heat exchanger of the present invention can take the following forms based on the above-mentioned configuration.

More specifically, the thin tube bundle can be divided in a flow direction of the blood channel, and a stack structure of a plurality of stages of the thin tube bundle units, each of the stages including the plurality of the heat transfer thin tubes, can be formed. In this case, it is preferred that the heat transfer thin tube headers are formed so that the heat medium liquid successively passes from the thin tube bundle unit in a downstream stage placed on a downstream side of the blood channel to the thin tube bundle unit in an upstream stage placed on an upstream side. This causes the flow of the heat medium liquid to be a counterflow with respect to the flow of liquid to be subjected to heat exchange, which is advantageous for enhancing the heat exchange efficiency. Further, it is preferred that the thin tube bundle is divided into three stages of the thin tube bundle units. In this case, it is preferred that a total number of the heat transfer thin tubes constituting the thin tube bundle unit in each stage is two or three layers. Further, it is preferred that the blood channel is formed in a cylindrical shape whose circumference is sealed with the seal member.

Further, in the case of a configuration in which the thin tube bundle is divided in a flow direction of the flood channel and a stack structure of a plurality of stages of the thin tube bundle units is formed, it is preferred that spacers are mounted between the plurality of stages of thin tube bundle units to provide respective intervals between the respective stages, and at least one of the flow chambers is partitioned into a plurality of flow compartments by a partition wall positioned so as to correspond to the interval, thereby forming a channel such that the heat medium liquid flowing in from the inlet port passes through the plurality of stages of thin tube bundle units successively via any one of the flow compartments and flows out of the outlet port via any other of the flow compartments.

Thus, if the structure in which the spacers are mounted and predetermined intervals are formed between the respective stages of the thin tube bundle units, the flow chamber formed by the heat transfer thin tube header can be divided easily. This can simplify the structure in which heat medium liquid passes through the plurality of stages of the thin tube bundle units in a desired order, and the structures of the inlet and outlet ports.

In the above-mentioned configuration, a pair of the spacers can be placed respectively in regions sealed with the seal member on both sides sandwiching the blood channel to form a pair. In this case, the pair of the spacers can be coupled with each other to be integrated.

Further, the thin tube bundle units can include thin tube row holding members holding an arrangement state of the plurality of the heat transfer thin tubes, and the spacers can be mounted between the thin tube row holding members opposed to each other between the stages of the adjacent thin tube bundle units.

Further, the flow chamber can be partitioned into the flow compartment corresponding to a single stage of the thin tube bundle unit positioned at an upstream end or a downstream end of the blood channel and the flow compartments corresponding to respective other pairs of stages of the thin tube bundle units, and the inlet port and the outlet port can be provided to the flow compartment corresponding to the single stage of the thin tube bundle unit.

It is preferred that the thin tube bundle units are formed in three stages, one of the heat transfer thin tube headers includes the flow compartment corresponding to the one stage of the thin tube bundle unit positioned at the upstream end of the blood channel and the flow compartment corresponding to the two stages of the thin tube bundle units on a downstream side, the other heat transfer thin tube header includes the flow compartment corresponding to the one stage of the thin tube bundle unit positioned at the downstream end of the blood channel and the flow compartment corresponding to the two stages of the thin tube bundle units on an upstream side, and the inlet port is provided in the flow compartment corresponding to the thin tube bundle unit at the downstream end and the outlet port is provided in the flow compartment corresponding to the thin tube bundle unit at the upstream end.

Further, in the case where the thin tube bundle is divided in a flow direction of the blood channel to form a stack structure of a plurality of stages of the thin tube bundle units, and spacers are mounted between the stages of the plurality of stages of thin tube bundle units to form predetermined intervals between the respective stages, it is preferred that, in a region inside the blood channel, an insertion member is placed in a gap formed by the interval between the thin tube bundle units so as to fill a part of a volume of the gap, and the insertion member has a channel communicating with the blood channel.

Thus, in the case of a simple structure in which the flow chamber can be divided by mounting the spacers, which allows the heat medium liquid to pass through a plurality of stages of thin tube bundle units successively in a desired order, the increase in volume of the blood channel is suppressed by placing the insertion member.

It is preferred that the insertion member includes a plurality of annular ribs arranged concentrically and connection ribs extending radially in a diameter direction of the annular ribs and connecting the respective annular ribs. In this case, it is preferred that the annular rib has an oval cross-sectional shape with a direction of the blood channel being a minor axis.

In the case of the above-mentioned configuration in which the flow chamber can be divided by mounting the spacers, which allows the heat medium liquid to pass through a plurality of stages of thin tube bundle units successively in a desired order, and further, the increase in volume of the blood channel is suppressed by placing the insertion member, a pair of the spacers can be placed respectively in the sealed regions on both sides sandwiching the blood channel, and the spacers and the insertion member can be made of materials different from each other.

Due to the configuration in which the insertion member and the spacers are made of different materials, the increase in volume of the blood stream caused by the spacers can be suppressed while the leakage of blood from the blood channel is avoided.

In this case, it is preferred that the medical heat exchanger includes a connecting portion connecting a plurality of the insertion members placed between the respective stages of the thin tube bundle units at a side edge of the thin tube bundle.

Alternatively, the medical heat exchanger can include a positioning member placed at a side edge of the thin tube bundle, and each of the plurality of the insertion members placed between the respective stages of the thin tube bundle units can have an engagement portion that is engaged with the positioning member in a part of a circumferential edge, and can be positioned with respect to the thin tube bundle by the engagement. In this case, the positioning member can be formed on an inner wall of the housing.

Further, the arrangement state of the heat transfer thin tubes in the thin tube bundle can be held by thin tube row holding members placed at both ends of the thin tube bundle, the spacers can be mounted between the thin tube row holding members opposed to each other between the adjacent stages of the thin tube bundle, a pair of bridge members further can be provided, which are made of the same material as that of the seal member and placed between a pair of the thin tube row holding members and the insertion member, and the bridge members can abut against the insertion member and the pair of the thin tube row holding members and can be sealed in the seal member.

Further, the thin tube bundle can be divided in a transverse direction with respect to a flow direction of the blood channel to form the plurality of groups of thin tube bundle units. In this case, it is preferred that the blood channel has a circular cross-section, the thin tube bundle is divided into three in the transverse direction with respect to the flow direction of the blood channel to form a center thin tube bundle unit and side thin tube bundle units positioned on both sides thereof and the heat transfer thin tube headers are formed so that the heat medium liquid first passes through the center thin tube bundle unit with a larger heat exchange area, and then, passes through the side thin tube bundle units.

A method for producing the medical heat exchanger with the above-mentioned configuration includes: a thin tube bundle unit formation step of forming the thin tube bundle units, using a thin tube row holding member holding an arrangement state of the heat transfer thin tubes; a thin tube bundle module formation step of forming a thin tube bundle module by stacking a plurality of the thin tube bundle units while placing spacers at both ends between respective stages and interposing an insertion member that fills a part of a gap between the thin tube bundle units between the respective stages in a center portion of the thin tube bundle units; and a sealing step of sealing the thin tube bundle module with the seal member so that the blood channel is formed in a region including the insertion member, with the insertion member having a channel communicating with the blood channel, while exposing both ends of the thin tube bundle. In the thin tube bundle module formation step, bridge members made of the same material as that of the seal member are placed between a pair of the thin tube row holding members and the insertion member so as to abut against the pair of the thin tube row holding members and the insertion member respectively, whereby the insertion member is held between the thin tube row holding members, and in the sealing step, the bridge members are sealed in the seal member.

An artificial lung device includes: the heat exchanger with any of the above-mentioned configurations; and an artificial lung having a blood channel that crosses a gas channel so as to perform gas exchange, wherein the heat exchanger and the artificial lung are stacked, and the blood channel of the heat exchanger and the blood channel of the artificial lung communicate with each other.

Hereinafter, a medical heat exchanger in an embodiment of the present invention will be described with reference to the drawings. The following embodiments are exemplary applications to an artificial lung device and will be described exemplifying a heat exchanger used for adjusting the temperature of blood collected from a patient.

Embodiment 1

Figure 1C:
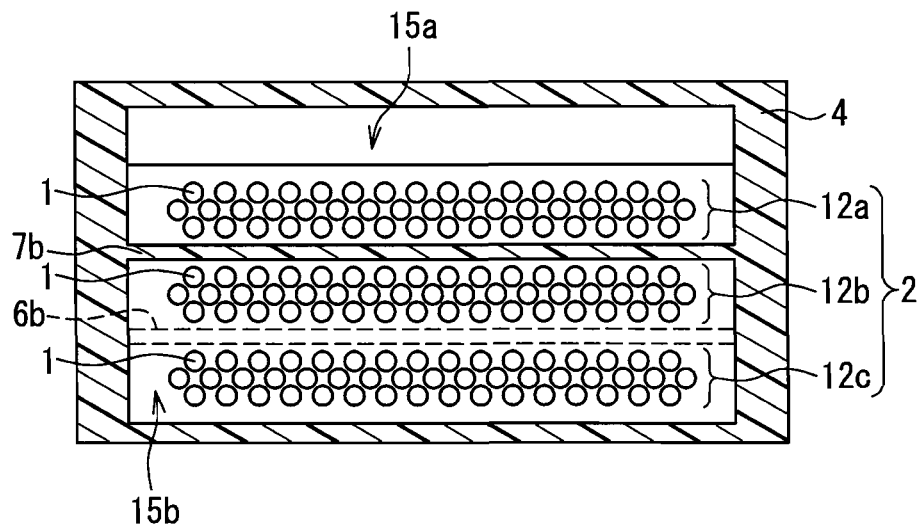
FIG. 1C is a cross-sectional view taken along the line B-B of the medical heat exchanger.

FIG. 1A is a plan view illustrating a medical heat exchanger in Embodiment 1. FIG. 1B is a cross-sectional view taken along the line A-A in FIG. 1A, and FIG. 1C is a cross-sectional view taken along the line B-B in FIG. 1A. The heat exchanger includes a thin tube bundle 2 composed of a plurality of heat transfer thin tubes 1 for distributing cool/warm water as heat medium liquid, seal members 3a-3c sealing the thin tube bundle 2, and a housing 4 containing these components.

A plurality of the heat transfer thin tubes 1 are arranged in parallel and stacked to form the thin tube bundle 2, and cool/warm water is allowed to flow through a lumen of each heat transfer thin tube 1. A blood channel 5 having a circular cross-section is formed in a center portion in a longitudinal direction of the thin tube bundle 2 in the seal member 3c at the center, and functions as a heat exchange region for letting blood to flow as the liquid to be subjected to heat exchange. When the blood passing through the blood channel 5 comes into contact with each outer surface of the heat transfer thin tube 1, heat exchange is performed. The seal members 3a, 3b at both ends expose both ends of the thin tube bundle 2.

The housing 4 has heat transfer thin tube headers, i.e., a cool/warm water inlet header 6 for introducing cool/warm water and a cool/warm water outlet header 7 for discharging the cool/warm water, bordering both ends of the thin tube bundle 2. Further, as illustrated in FIG. 1B, the housing 4 is provided with a blood inlet port 8 and a blood outlet port 9, positioned at upper and lower ends of the blood channel 5. The cool/warm water inlet header 6 and the cool/warm water outlet header 7 respectively are provided with a cool/warm water inlet port 6a and a cool/warm water outlet port 7a. Further, gaps 10 are provided respectively between the seal members 3a-3c, and the housing 4 is provided with leaked liquid discharge holes 11 corresponding to the gaps 10.

As illustrated in FIG. 1B, the cool/warm water inlet header 6 and the cool/warm water outlet header 7 form flow chambers (including an upper flow compartment 14a, a lower flow compartment 14b, an upper flow compartment 15a, a lower flow compartment 15b) that are hollow chambers respectively surrounding both ends of the thin tube bundle 2 exposed from the seal members 3a, 3b at both ends. Thus, the cool/warm water that is to be introduced and discharged all flows via the flow chambers formed by the cool/warm water inlet header 6 and the cool/warm water outlet header 7.

In the above-mentioned configuration, the blood is allowed to flow in the blood channel 5 from the blood inlet port 8 and flow out of the blood outlet port 9. Simultaneously, the cool/warm water is allowed to flow in the thin tube bundle 2 from the cool/warm water inlet header 6 and flow out of the cool/warm water outlet header 7. Thus, heat exchange is performed between the blood and the cool/warm water in the blood channel 5. Further, in any of the case where the blood leaks and the case where the cool/warm water leaks, the seal leakage can be detected immediately through the leaked liquid discharge holes 11, and the blood contamination can be prevented, in the same way as in the conventional example.

The present embodiment is characterized in that, as illustrated in FIG. 1B, the thin tube bundle 2 is divided into three stages of first to third thin tube bundle units 12a-12c, each including the three-layered heat transfer thin tubes 1. More specifically, each of the first to third thin tube bundle units 12a-12c has a configuration in which the heat transfer thin tubes 1 are stacked in three layers. Then, the first to third thin tube bundle units 12a-12c are stacked to form the thin tube bundle 2. Spacers 13 are placed between the respective stages of the first to third thin tube bundle units 12a-12c to provide intervals with a predetermined length.

Providing the intervals using the spacers 13 facilitates the partition of the flow chambers in the cool/warm water inlet header 6 and the cool/warm water outlet header 7 into a plurality of flow compartments as described in Embodiment 2. It should be noted that the intervals also can be provided between the respective stages of the first to third thin tube bundle units 12a-12c without using the spacers 13. For example, the same structure can be obtained by using a jig holding the first to third thin tube bundle units 12a-12c with intervals placed between the respective stages when forming a sealing structure with the seal members 3a-3c.

In the cool/warm water inlet header 6, the flow chamber therein is partitioned into the upper flow compartment 14a and the lower flow compartment 14b with a partition wall 6b. In the upper flow compartment 14a, the ends of the first and second thin tube bundle units 12a, 12b are placed, and in the lower flow compartment 14b, the end of the third thin tube bundle unit 12c is placed. Further, the flow chamber in the cool/warm water outlet header 7 is partitioned into the upper flow compartment 15a and the lower flow compartment 15b with a partition wall 7b. In the upper flow compartment 15a, the end of the first thin tube bundle unit 12a is placed, and in the lower flow compartment 15b, the second and third thin tube bundle units 12b, 12c are placed.

The functions and effects obtained by the heat exchanger configured as described above will be described below. Cool/warm water introduced from the cool/warm water inlet port 6a to the lower flow compartment 14b of the cool/warm water inlet header 6 flows through lumens of the heat transfer thin tubes 1 of the third thin tube bundle unit 12c and flows in the lower flow compartment 15b of the cool/warm water outlet header 7. Further, the cool/warm water enters the heat transfer thin tubes 1 of the second thin tube bundle unit 12b and flows therethrough to reach the upper flow compartment 14a of the cool/warm water inlet header 6. Then, the cool/warm water enters the heat transfer thin tubes 1 of the first thin tube bundle unit 12a and flows therethrough to reach the upper flow compartment 15a of the cool/warm water outlet header 7 and flow out of the cool/warm water outlet port 7a.

Thus, the cool/warm water inlet header 6 and the cool/warm water outlet header 7 are configured so that the cool/warm water to be introduced passes through three stages of the third to first thin tube bundle units 12c-12a successively. The configuration in which the cool/warm water to be introduced passes through a plurality of groups of divided thin tube bundle units will be referred to as a divided flow hereinafter. In contrast, the configuration in which the cool/warm water to be introduced flows in all the heat transfer thin tubes 1 at a time in the cool/warm water inlet header 6 as in the conventional example will be referred to as a simultaneous flow.

The channel cross-sectional area through which cool/warm water passes becomes smaller as a result of adopting the divided flow. Therefore, assuming that the flow rate of cool/warm water is the same, the flow speed of the cool/warm water flowing through each heat transfer thin tube 1 of the first to third thin tube bundle units 12a-12c can be increased, compared with that of the simultaneous flow. This can reduce the film resistance in an inner wall of the heat transfer thin tube 1 to enhance heat exchange efficiency. In the conventional simultaneous flow, although the heat exchange efficiency can be enhanced by increasing the supply flow rate from the supply source of cool/warm water, it is actually difficult to increase the flow rate of the supply source of cool/warm water on a medical facility side. Therefore, enhancing the heat exchange efficiency as in the present embodiment is very effective from the practical point of view.

Further, the embodiment illustrated in FIG. 1B adopts a turnback structure in a vertical direction (perpendicular direction), i.e., a structure in which the thin tube bundle 2 is divided in a flow direction of blood (i.e., a vertical direction) to form a plurality of stages of thin tube bundle units. Further, the cool/warm water flows from the thin tube bundle unit 12c in the lowest stage placed on the downstream side of the blood channel 5 to the upstream stage through the thin tube bundle unit 12b and the thin tube bundle unit 12a successively. This means that the flow of the cool/warm water is formed to be a counterflow with respect to a blood flow, which is effective for obtaining higher heat exchange efficiency.

Figure 2:
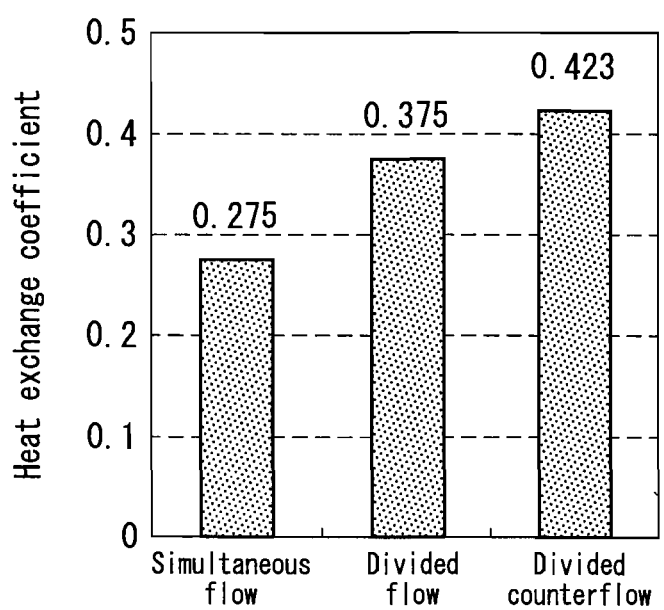
FIG. 2 is a diagram illustrating a relationship between the form of division of a thin tube bundle and the heat exchange coefficient.

FIG. 2 illustrates the results obtained by conducting an experiment regarding the effect that the heat exchange efficiency is enhanced by the divided flow as described above. The "divided parallel flow" and the "divided counterflow" in FIG. 2 indicate the case of the divided flow according to the present embodiment. The "divided counterflow" is the case where the thin tube bundle is divided along a flow direction of heat medium liquid and the heat medium liquid is set to be a counterflow as illustrated in FIG. 1B. The "divided parallel flow" refers to the case where the heat medium liquid is set to form a parallel flow whose direction is the same as that of the blood flow, although the form of division is the same. In both the cases, an opening diameter of the blood channel 5 was set at 70 mm, and the number of layers of the heat transfer thin tubes 1 was set at 12.

It is understood from FIG. 2 that the heat exchange efficiency in the case of the divided parallel flow and the divided counterflow, both of which are divided flow, is higher than that of the simultaneous flow. The reasons for this are as follows. Since the flow speed of the cool/warm water flowing through the heat transfer thin tubes 1 is larger in the divided flow, the film resistance is reduced. Further in the case of the divided counterflow, the difference in temperature between the heat medium liquid and the blood can be kept high even on the blood downstream side, and hence, the result that the heat exchange efficiency is higher than that in the case of the divided parallel flow is obtained. The heat exchange efficiency in the case of the divided parallel flow is larger by 36%, and the heat exchange efficiency in the case of the divided counterflow is larger by 54%, compared with that in the case of the simultaneous flow.

Figure 3:
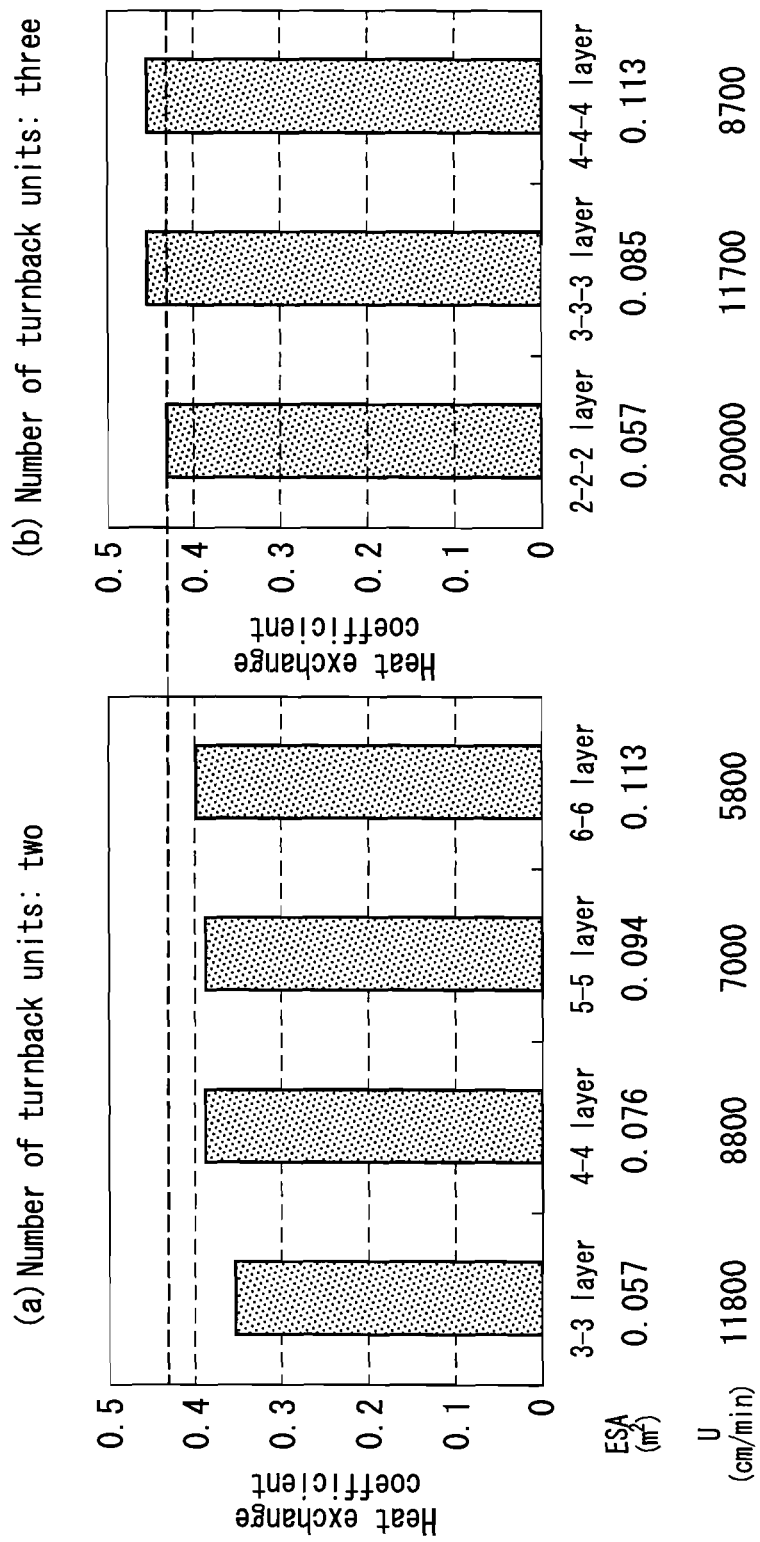
FIG. 3 is a diagram illustrating a relationship between the turnback structure of the medical heat exchanger and the heat exchange coefficient in Embodiment 1.

Next, FIG. 3 illustrates the results obtained by considering the appropriate number of layers of the thin tube bundle units and the appropriate number of layers of the heat transfer thin tubes 1 constituting each thin tube bundle unit in the case where the thin tube bundle 2 is divided in a vertical direction to form a plurality of layers of thin tube bundle units as illustrated in FIG. 1B.

In FIG. 3, (a) illustrates the measurement results of heat exchange efficiency in the case where the number of stages of the thin tube bundle units is two, i.e., the number of stages at which the flow of the cool/warm water is turned back is two, and the heat transfer thin tubes constituting the thin tube bundle unit in each stage is three layers (number of stacked layers), four layers, five layers, and six layers. In FIG. 3, (b) illustrates the measurement results of the heat exchange efficiency in the case where the number of stages of the turnback thin tube bundle units is three, and the heat transfer thin tubes constituting the thin tube bundle unit in each stage is two layers, three layers, and four layers. ESA and U shown in a lower portion of a horizontal axis indicate an effective surface area and a flow speed of a heat medium, respectively. It is understood from FIG. 3 that higher heat exchange efficiency is likely to be obtained in the case (b) where the number of stages of the turnback thin tube bundle units is three, compared with the case (a) where the number of stages is two.

When the number of stages of the turnback thin tube bundle units is three, the heat exchange efficiency is slightly degraded in the case where the number of layers of the heat transfer thin tubes constituting a thin tube bundle unit is two, i.e., the configuration of a 2-2-2 layer at a left end in (b) of FIG. 3, compared with the case where the number of layers is three and four. However, high heat exchange efficiency can be obtained, compared with the case of two stages. Further, the total number of layers of the heat transfer thin tubes in three stages is six, and compared with the configuration of a 3-3 layer in two stages having the number of heat transfer thin tube layers corresponding thereto, sufficiently high heat exchange efficiency is obtained. The same number of layers of the heat transfer thin tubes means that a blood priming volume is substantially the same. Thus, it is understood that the heat exchange efficiency can be enhanced while the blood priming volume is suppressed according to the configuration of the 2-2-2 layer.

It also is understood that no significant difference is found in heat exchange efficiency between the case where the number of layers of the heat transfer thin tubes constituting a thin tube bundle unit is three and the case where the number of layers of the heat transfer thin tubes constituting a thin tube bundle unit is four, when the number of stages is three. Four or more stages are excessive for performance, and in this case, a flow rate does not increase due to an increase in a pressure loss. Considering this result, it is understood that the most preferred structure from the practical point of view can be obtained when the thin tube bundle units, each being formed of three layers of heat transfer thin tubes, are stacked in three stages.

Further, in the case of an odd-number turnback structure as in a three-stage turnback structure, the cool/warm water inlet port 6a and the cool/warm water outlet port 7a can be distributed to both ends of the thin tube bundle 2, and hence, the port layout has a good balance.

Although not shown in the above-mentioned figures, the housing 4 can be configured, for example, in such a manner that the housing 4 is formed of a housing bottom portion and a housing upper portion, which are integrated with the thin tube bundle 2 and the like contained therein. Alternatively, the housing 4 can be configured in such a manner that the housing 4 contains only the thin tube bundle 2 and the seal members 3a-3c, while the cool/warm water inlet header 6 and the cool/warm water outlet header 7 are separated from the housing 4.

In the above description, the structures of the cool/warm water inlet header and the cool/warm water outlet header in the case where the thin tube bundle units have three stages are illustrated. However, the cool/warm water inlet header and the cool/warm water outlet header can be configured similarly even with another number of stages. More specifically, flow compartments corresponding to one stage of the thin tube bundle unit positioned at an upstream end or a downstream end are provided necessarily. Thus, the flow compartments are formed at least in one of the cool/warm water inlet header and the cool/warm water outlet header. Further, the flow compartment is partitioned so as to correspond to the thin tube bundle units of the respective other pairs of the stages. Each of the inlet port and the outlet port is provided with respect to the flow compartment corresponding to one stage of the thin tube bundle unit. This forms a channel in such a manner that heat medium liquid flowing in from the inlet port passes through a plurality of stages of the thin tube bundle units successively and flows out of the outlet port.

In the present embodiment, for example, a metal material such as stainless steel is preferred as a material constituting the heat transfer thin tube 1. As a material for the housing 4, for example, a resin material such as polycarbonate resin that is transparent and has excellent fracture strength can be used. As a resin material for forming the seal members 3a-3c, for example, thermosetting resin such as silicon resin, polyurethane resin, and epoxy resin can be used. Of them, it is preferred to use polyurethane resin or epoxy resin due to the excellent adhesion with respect to the material (e.g., a metal material) constituting the heat transfer thin tube 1 and the material constituting the housing 4.

Embodiment 2

A medical heat exchanger in Embodiment 2 will be described with reference to FIGS. 1A-1C in the same way as in Embodiment 1. In the present embodiment, a configuration will be described, which has a vertical turnback structure including a plurality of stages of thin tube bundle units stacked in a direction of a blood flow, i.e., a vertical direction and which uses the spacers 13 as members for forming intervals between the respective stages of the first to third thin tube bundle units 12a-12c. The other configuration is similar to that of Embodiment 1, and hence, the repetition of the descriptions will be omitted.

As described in Embodiment 1, in order to form a vertical turnback structure, it is necessary to partition the flow chamber of the cool/warm water inlet header 6 into the upper flow compartment 14a and the lower flow compartment 14b with the partition wall 6b, and partition the flow chamber of the cool/warm water outlet header 7 into the upper flow compartment 15a and the lower flow compartment 15b with the partition wall 7b. For this purpose, it is desired to form intervals between the respective stages of the first to third thin tube bundle units 12a-12c with the spacers 13. This is because, by placing ends of the partition wall 6b and the partition wall 7b so as to correspond to the intervals between the respective stages of the first to third thin tube bundle units 12a-12c, the flow chambers can be partitioned easily.

Figure 4A:
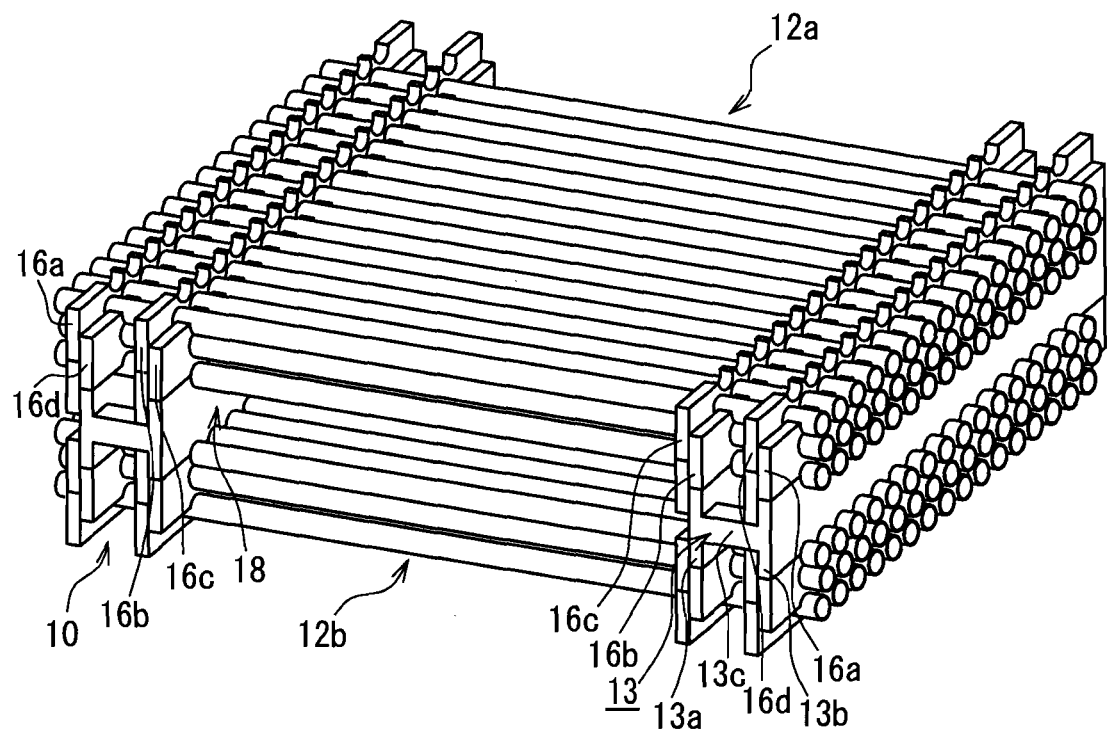
FIG. 4A is a perspective view of a module with a spacer attached between thin tube bundle units, used in a medical heat exchanger in Embodiment 2.
Figure 4B:
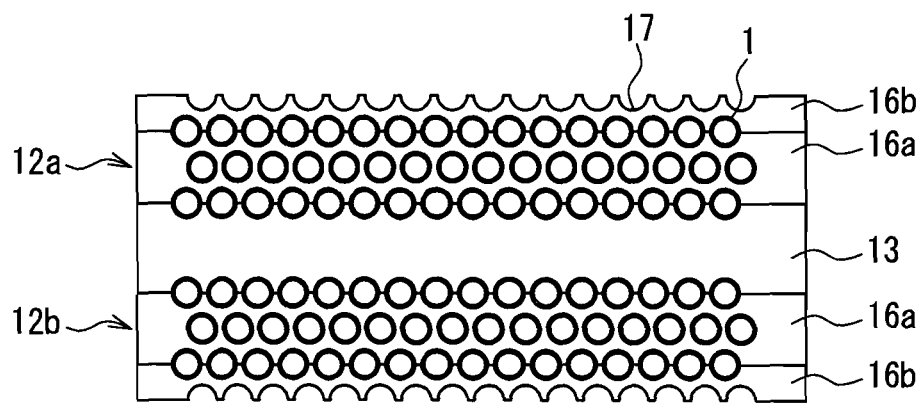
FIG. 4B is a front view of the module.

An example of the form of the spacers 13 will be described with reference to FIG. 4A-FIG. 5. FIG. 4A is a perspective view illustrating the form of a module with spacers mounted between the thin tube bundle units. For convenience of illustration, only two stages of the first and second thin tube bundle units 12a, 12b are illustrated among three stages of the thin tube bundle units. For convenience of illustration, the size in a vertical direction is illustrated in an enlarged state, compared with FIG. 1B. In the subsequent other figures, the size in the vertical direction will be illustrated in an enlarged state similarly. FIG. 4B is a front view of the module.

As illustrated in FIG. 4A, the thin tube bundle units 12a, 12b respectively have a configuration in which a plurality of heat transfer thin tubes 1 are bound by thin tube row holding members 16a-16d arranged at four portions in an axis direction of the heat transfer thin tubes 1. The spacers 13 are mounted between the thin tube row holding members 16a-16d between the stages of the thin tube bundle units 12a, 12b.

One set of the thin tube row holding members 16a-16d binds one row (layer) of a thin tube row. The bound state is illustrated in the perspective view of FIG. 5A. FIG. 5B is a front view thereof. A plurality of the heat transfer thin tubes 1 (16 in the example of FIG. 5A) arranged in a row in parallel to each other are held by the thin tube row holding members 16a-16d, and thus, one layer of a heat transfer thin tube group is formed. The thin tube row holding members 16a-16d respectively are formed in a band shape traversing the heat transfer thin tubes 1, and the heat transfer thin tubes 1 pass through the thin tube row holding members 16a-16d. The heat transfer thin tube group in such a form can be formed by so-called insert molding of injecting resin into a die in which a plurality of the heat transfer thin tubes 1 are arranged to form the thin tube row holding members 16a-16d. Upper and lower surfaces of the thin tube row holding members 16a-16d are provided with a plurality of thin tube receiving concave portions 17 in which the heat transfer thin tubes 1 in another adjacent heat transfer thin tube group can be fitted.

Figure 5A:
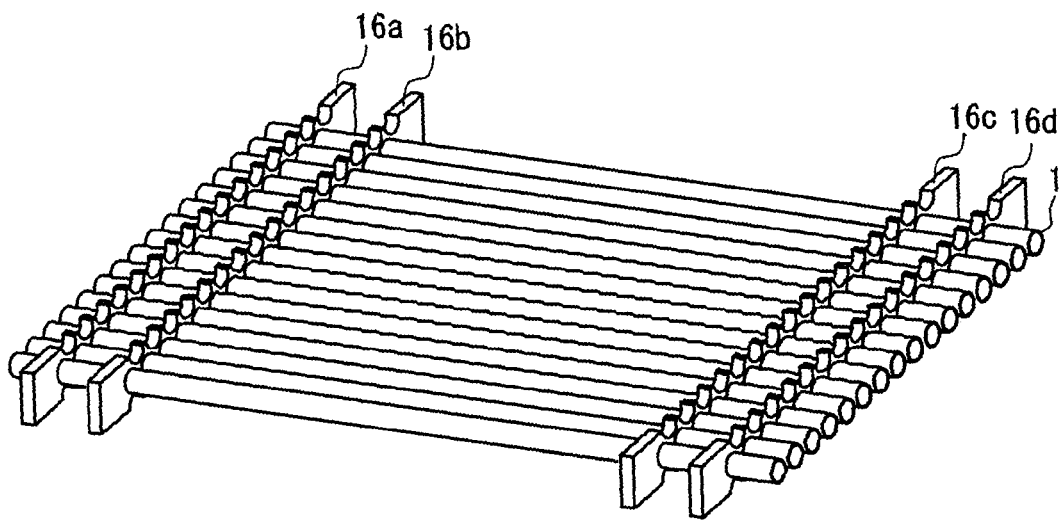
FIG. 5A is a perspective view of a unit thin tube row for composing the module.
Figure 5B:
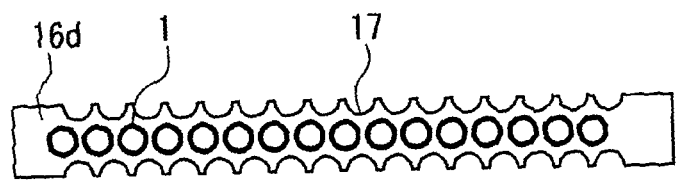
FIG. 5B is a front view of the unit thin tube row.

The thin tube bundle units 12a, 12b illustrated in FIG. 4A respectively are formed by stacking three layers of the heat transfer thin tube groups of FIG. 5A. For stacking, the heat transfer thin tubes 1 constituting each heat transfer thin tube group are fitted in the thin tube receiving concave portions 17 provided in the thin tube row holding members 16a-16d in upper and lower adjacent other heat transfer thin tube groups. Therefore, the thin tube row holding members 16a-16d are placed so as to be shifted from each other alternately for the respective upper and lower adjacent layers. Further, the thin tube row holding members 16a-16d are placed as a pair in each end region of the heat transfer thin tubes 1. More specifically, the thin tube row holding members 16a, 16b are placed close to each other at one end and the thin tube row holding members 16c, 16d are placed close to each other at the other end. Due to such an arrangement, the gaps 10 illustrated in FIG. 1B, etc. are formed between the thin tube row holding members 16b, 16d at both ends.

Between the stages of the thin tube bundle units 12a, 12b, the spacers 13 are inserted between the thin tube row holding members 16a-16d, and thus, an interval 18 (FIG. 4A) with a predetermined size is formed. The spacer 13 is composed of insertion portions 13a, 13b and a connecting portion 13c connecting the insertion portions 13a, 13b. The interval 18 between the thin tube bundle units 12a, 12b is maintained by interposing the insertion portions 13a, 13b between the upper and lower thin tube row holding members 16a-16d.

Figure 6:
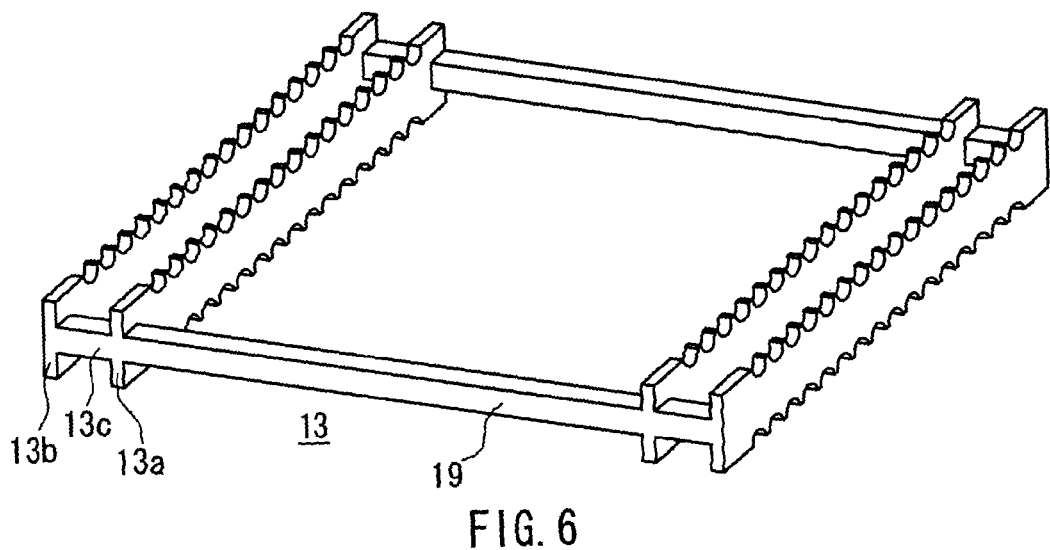
FIG. 6 is a perspective view illustrating an exemplary form of the spacer.

The spacers 13 are used as a pair of separated spacers 13, provided individually at both ends of the heat transfer thin tubes 1. In contrast, for example, a structure illustrated in FIG. 6 also can be used. More specifically, a pair of spacers 13 are integrated by coupling frames 19. This facilitates the handling in a production step. As the material for the spacers 13, for example, polycarbonate resin can be used.

Embodiment 3

Figure 7A:
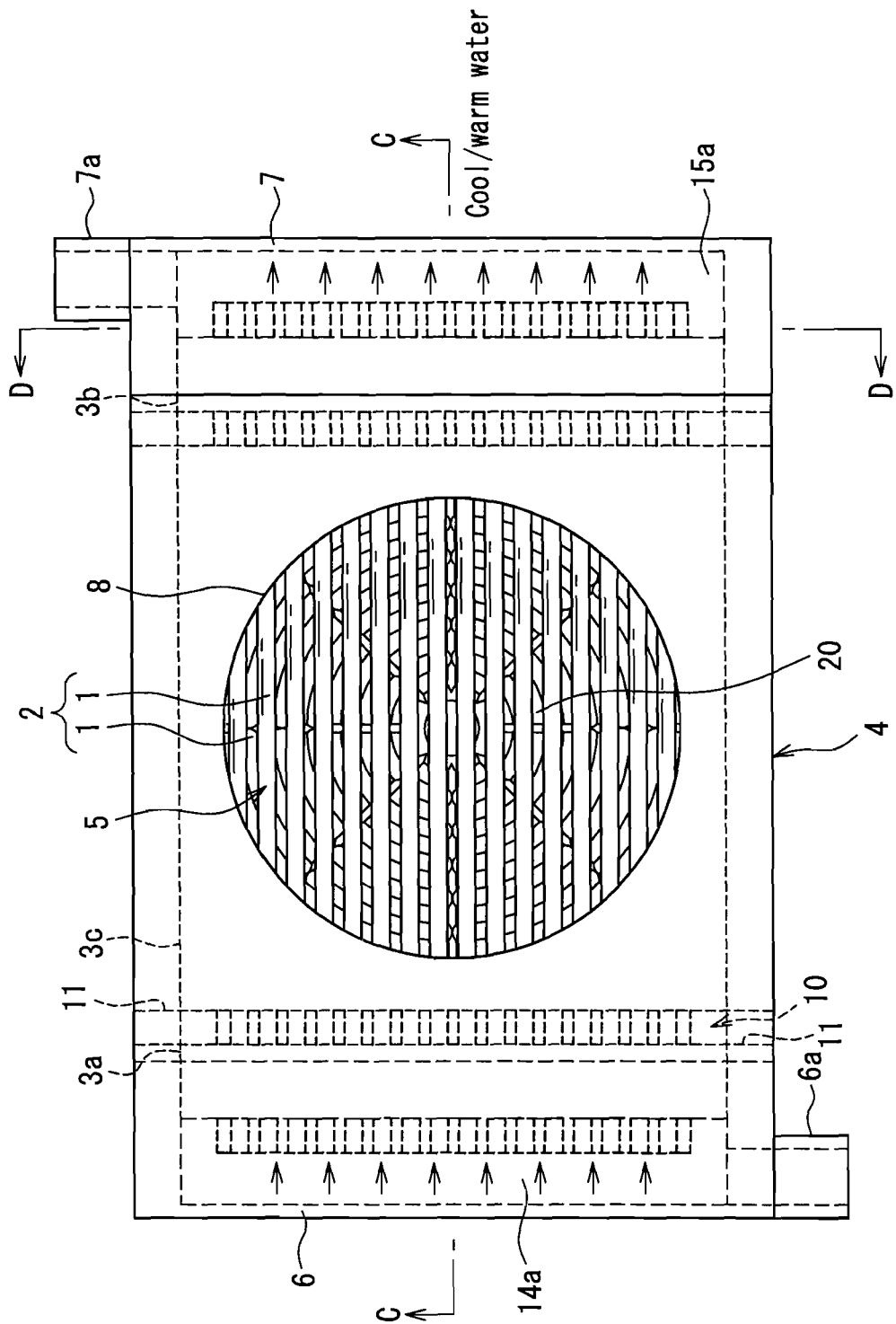
FIG. 7A is a top view illustrating a configuration of a medical heat exchanger in Embodiment 3.
Figure 7B:
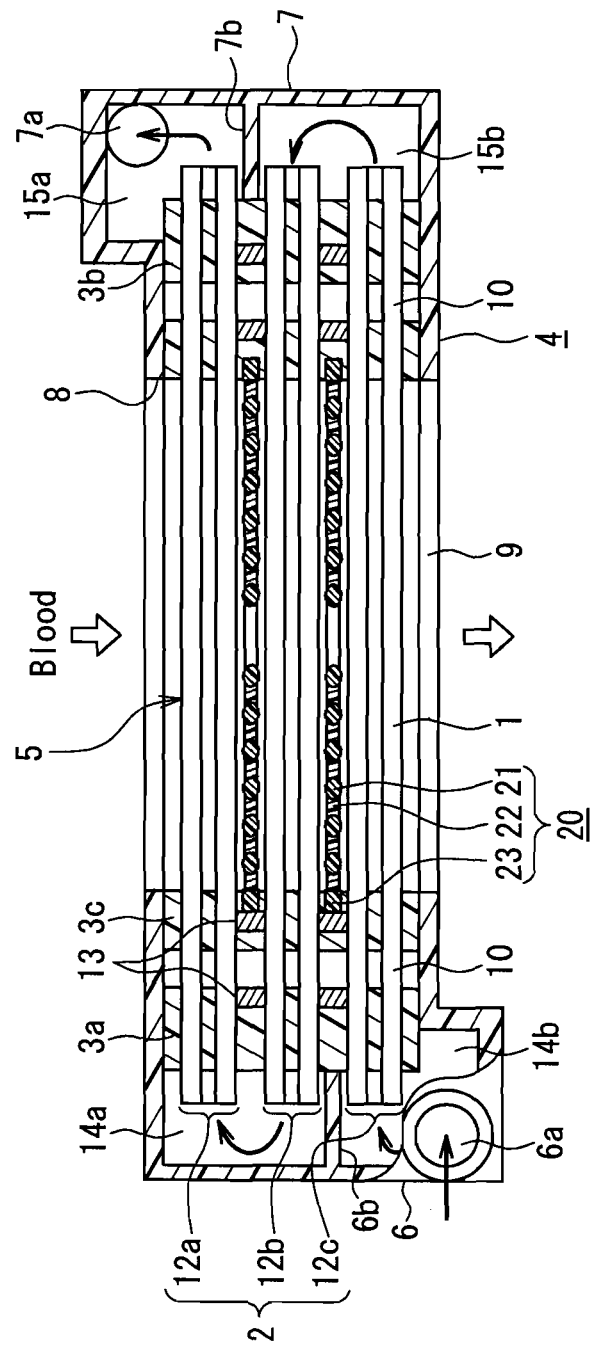
FIG. 7B is a cross-sectional view taken along the line C-C of the medical heat exchanger.

FIG. 7A is a plan view illustrating a medical heat exchanger in Embodiment 3. FIG. 7B is a cross-sectional view taken along the line C-C in FIG. 7A. The shape of the D-D cross-section in FIG. 7A is the same as that in Embodiment 1 illustrated in FIG. 1C. The feature of the present embodiment lies in that insertion members 20 are placed between the respective stages of the first to third thin tube bundle units 12a-12c in the blood channel 5, as illustrated in FIG. 7B. Thus, the elements similar to those in Embodiments 1 and 2 are denoted with the same reference numerals as those therein, and repeated descriptions thereof will be omitted.

As described in Embodiment 2, if intervals with a predetermined length are formed between the respective stages by inserting the spacers 13 between a plurality of stages of the thin tube bundle units 12a-12c, a simple configuration can be realized in which cool/warm water passes through the respective thin tube bundle units 12a-12c successively in a desired order. Even in the case of using such spacers 13, in a region of the seal members 3a-3c sealing the thin tube bundle 2, the material for the seal members 3a-3c fills a portion corresponding to the interval between each stage, and hence, a gap will not remain.

On the other hand, in the region in the blood channel 5, gaps corresponding to the intervals 18 remain between the respective stages of the first to third thin tube bundle units 12a-12c when the spacers 13 are inserted. The gap causes the priming volume of blood to increase in the blood channel 5, and therefore, in the present embodiment, the insertion member 20 is placed in the gap as illustrated in FIG. 7B. By placing the insertion member 20, parts of the gaps between the respective stages of the thin tube bundle units 12a-12c are filled and the volume thereof is reduced, and hence, the increase in a blood priming volume can be suppressed.

Figure 8A:
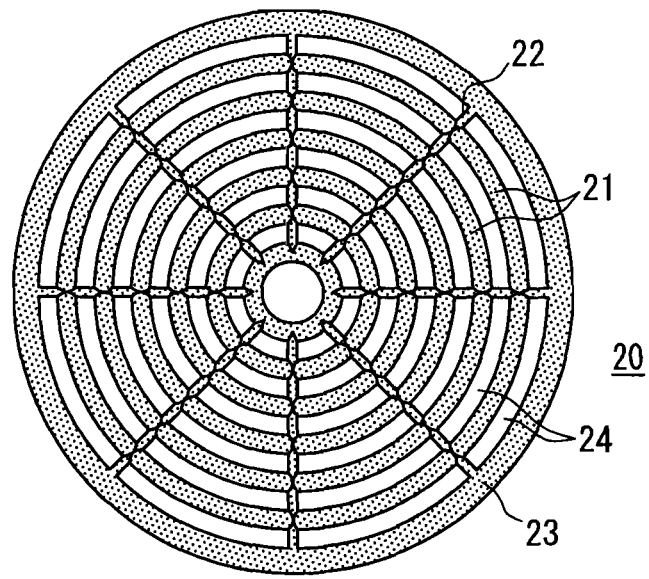
FIG. 8A is a plan view illustrating an insertion member used in the heat exchanger.

As FIG. 8A illustrates a planar shape, the insertion member 20 is composed of a plurality of annular ribs 21 arranged concentrically and connection ribs 22 extending radially in a diameter direction of the annular ribs 21 and connecting the annular ribs 21. The annular rib 21 on the outermost circumference is supported by an annular frame 23, and a portion of the annular frame 23 is sealed in the seal members 3a to 3c. Portions of the connection ribs 22 illustrated in FIG. 8A correspond to the clearances 24 between the annular ribs 21. The blood channel 5 passes through the insertion member 20 in the portions corresponding to the clearances 24, and thus, the continuity of the channel is kept.

Figure 8B:
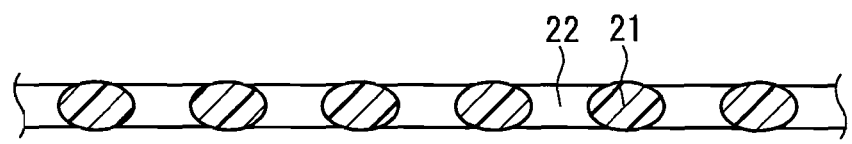
FIG. 8B is a partial cross-sectional view of the insertion member.

FIG. 8B is a cross-sectional view illustrating a part of the insertion member 20. The annular rib 21 has an oval cross-section with the direction of the blood channel 5 being a minor axis. By inserting the insertion member 20 with the above-mentioned configuration, the effect of decreasing a blood priming volume can be obtained sufficiently without decreasing heat exchange efficiency.

By placing the insertion member 20 as in the present embodiment, air bubbles originally present in the gaps are likely to be removed, compared with the case where only the gaps are present between the respective stages of the first to third thin tube bundle units 12a-12c, in addition to the effect of reducing a blood priming volume in the blood channel 5. When air bubbles are removed, the heat exchange efficiency also is enhanced.

Although placing the insertion member 20 inevitably decreases the heat exchange efficiency to some degree, the shape of the insertion member 20 is determined so that the overlapping between the heat transfer thin tubes 1 and the insertion members 20 is minimized, in order to suppress the decrease in heat exchange efficiency. Forming the insertion member 20 of the concentric annular ribs 21 as illustrated in FIG. 8A was effective for adjusting the balance between the reduction in a blood priming volume and the maintenance of heat exchange efficiency in a satisfying range.

Figure 9:
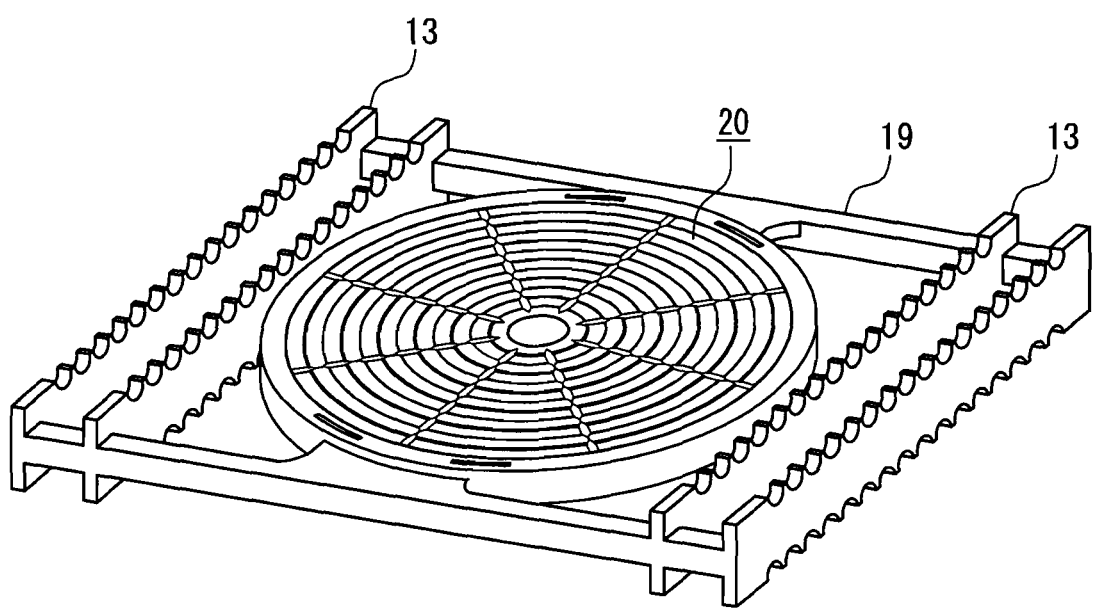
FIG. 9 is a perspective view illustrating another exemplary form of the insertion member.

Although the insertion member 20 can be produced separately from the spacers 13, the insertion member 20 also can be integrated with the spacers 13 as illustrated in FIG. 9. More specifically, a pair of the spacers 13 are integrated by the coupling frames 19, and further, the insertion member 20 and the coupling frames 19 are connected to each other. Such an integrated structure facilitates the operation for assembling the first to third thin tube bundle units 12a-12c integrally. As the insertion members 20, for example, a material similar to that for the spacers 13 can be used.

Next, the experimental results obtained by checking the decrease in heat exchange efficiency due to the placement of the insertion members between the stages of the thin tube bundle units will be described. For comparison with the insertion member in the present embodiment illustrated in FIG. 9, heat exchangers of samples A-E with the insertion members adjusted as follows were produced.

(A) The heat transfer thin tubes 1 are placed between the stages of the thin tube bundle units as insertion members (no cool/warm water is allowed to flow).

(B) The insertion members 20 of the present embodiment illustrated in FIG. 9 are placed.

Figure 10A:
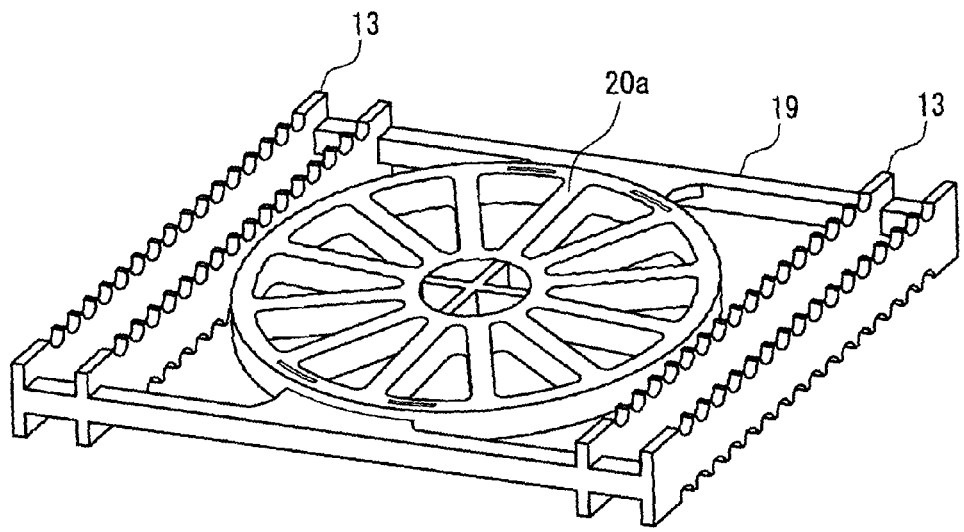
FIG. 10A is a perspective view illustrating the shape of an insertion member in a comparative example with respect to the insertion member.

(C) The insertion members 20a in a shape illustrated in FIG. 10A are placed.

(D) Gaps are left as they are without placing the insertion members.

Figure 10B:
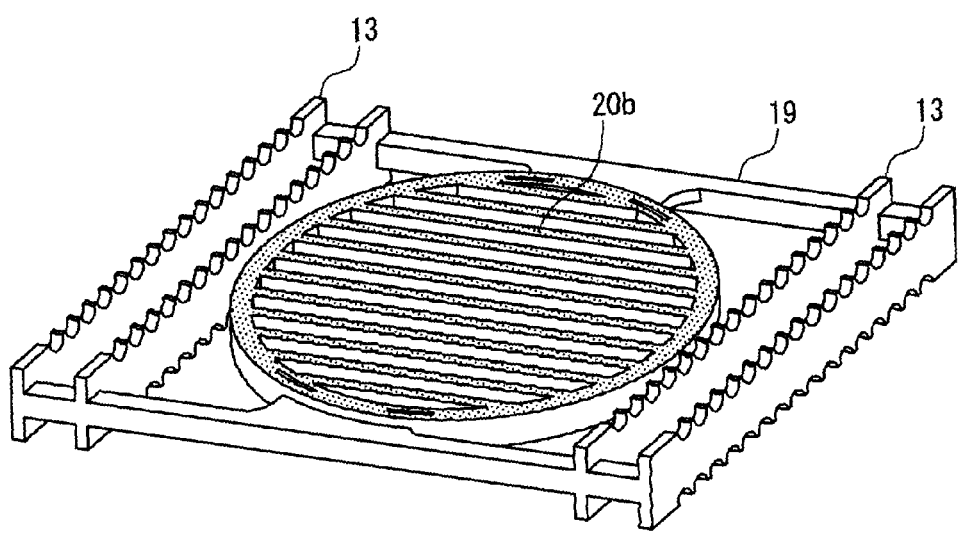
FIG. 10B is a perspective view illustrating the shape of an insertion member in another comparative example.

(E) The insertion members 20b in a shape illustrated in FIG. 10B are placed.

The sample A has an ideal form; however, the cost thereof is high. The samples B, C, and E were compared with each other under the condition that the filling ratio based on the volume of the insertion members is the same. The insertion member 20a illustrated in FIG. 10A is composed of only ribs in a diameter direction, and the insertion member 20b illustrated in FIG. 10B is composed of only linear ribs.

Figure 11:
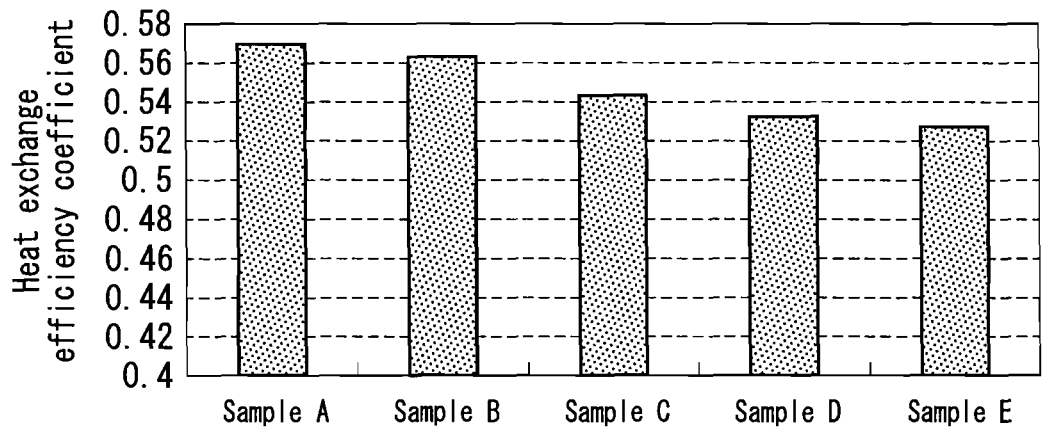
FIG. 11 is a diagram illustrating a heat exchange efficiency coefficient of a heat exchanger in the case of using various insertion members.

FIG. 11 illustrates the results obtained by checking a heat exchange efficiency coefficient of each sample. From the results, the following is understood: there is no substantial difference in results between the sample B in which the insertion members of the present embodiment are placed and the sample A, whereas the decrease in a heat exchange efficiency coefficient is large in the samples C, D, and E.

The reason for a large decrease in heat exchange efficiency coefficient in the case of the samples C and E is that the number of the overlapping portions between the insertion members and the heat transfer thin tubes is large in terms of a shape. More specifically, the insertion members block a blood flow, and the blood flow along the outer surface of the heat transfer thin tubes is limited.

As described above, by selecting the shape of the insertion member 20 appropriately, the decrease in heat exchange efficiency is suppressed in a range that has no practical problem and the blood priming volume in a blood channel can be reduced.

Embodiment 4

The basic configuration of a medical heat exchanger in Embodiment 4 is the same as that in Embodiment 3, and thus, the planar shape and cross-sectional shape thereof are similar to those illustrated in FIGS. 7A, 7B, and 1C. The feature of the present embodiment lies in that a separate structure in which the insertion members 20 and the spacers 13 are separated is adopted, and an improvement suitable for the separate structure is added thereto. Thus, the elements similar to those in Embodiment 3 are denoted with the reference numerals similar to those therein, and repeated descriptions thereof will be omitted.

Figure 12:
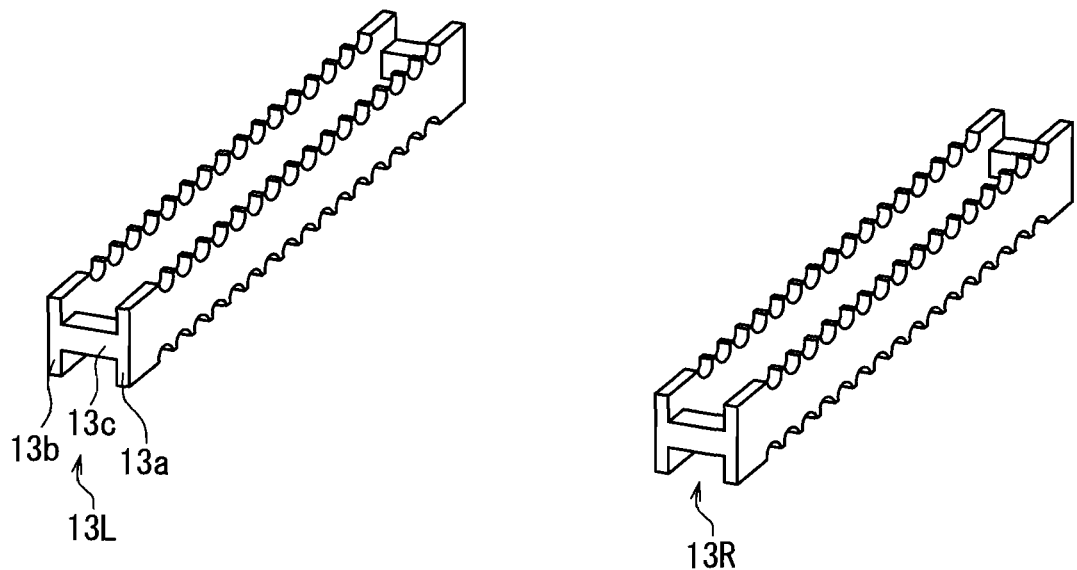
FIG. 12 is a perspective view illustrating the form of a spacer of a medical heat exchanger in Embodiment 4.

In the present embodiment, the spacers 13 are placed separately at both ends of the thin tube bundle units 12a, 12b. FIG. 12 illustrates a pair of spacers 13R, 13L placed separately at both ends of the thin tube bundle units 12a, 12b.

When the spacers 13 are mounted, gaps are formed between the respective stages of the first to third thin tube bundle units 12a-12c in a region in the blood channel 5. In order to suppress the increase in a blood priming volume in the blood channel 5 by the gaps, the insertion members 20 are placed so as to fill the gaps between the respective stages.

The insertion members 20 are placed between the respective stages. Therefore, if the insertion members 20 are integrated with the spacers 13, the operation of assembling the insertion members 20 and the spacers 13 integrally in combination with the first to third thin tube bundle units 12a-12c becomes easy. In contrast, the separate structure in which the insertion members 20 and the spacers 13 are placed separately renders the assembly operation cumbersome; however, it also has an advantage.

More specifically, in a structure in which the insertion member 20 is connected to the coupling frames 19 to be integrated with the spacers 13 as illustrated in FIG. 9, there is a possibility that liquid may flow through an interface between the coupling frames 19 and the seal members. In this case, the blood channel 5 is contaminated. In contrast, if the insertion member 20 and the spacers 13 are separate, the outer edge of the insertion member 20 is buried in the seal members, and hence, the possibility that the contamination may spread to the blood channel through the interface between the insertion member 20 and the seal members can be avoided. Even in the case where heat medium liquid leaks in an area of the spacers 13 or the coupling frames 19 of the spacers 13, the spread of the contamination to the blood channel can be blocked since the insertion member 20 and the coupling frames 19 are formed of separate members.

On the other hand, in the case where the insertion members 20 are separate from the spacers 13, when the insertion members 20 and the spacers 13 in combination with the first to third thin tube bundle units 12a-12c are sealed with the seal members 3a-3c, a structure for positioning the insertion members 20 with respect to the blood channel 5 is required.

Figure 13A:
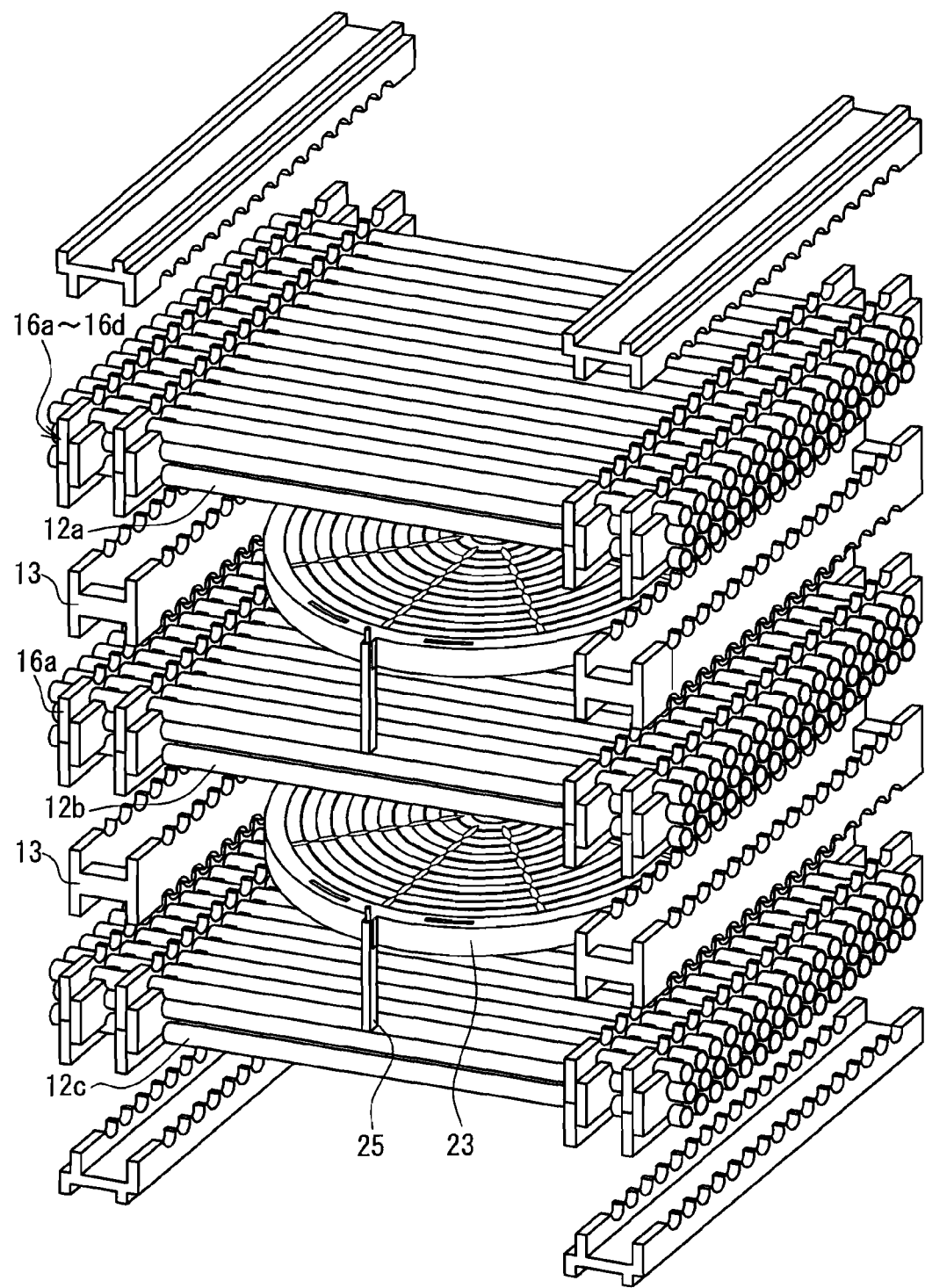
FIG. 13A is an exploded perspective view illustrating a positioning structure of the insertion member.

FIG. 13A is an exploded perspective view illustrating an example of a positioning structure of the insertion member 20. The stack structure (including three stages of the first to third thin tube bundle units 12a-12c) similar to that illustrated in FIG. 4A is illustrated. Intervals are kept between the first to third thin tube bundle units 12a-12c with the spacers 13 interposed between the upper and lower thin tube row holding members 16a-16d. In a region where the blood channel 5 is formed by the seal members 3a-3c (see FIG. 7B), the insertion members 20 are inserted. The insertion member 20 has a structure as illustrated in FIG. 8A, and the connecting portion 25 (see FIG. 13A) is formed at the annular frame 23 on each outer circumference.

Figure 13B:
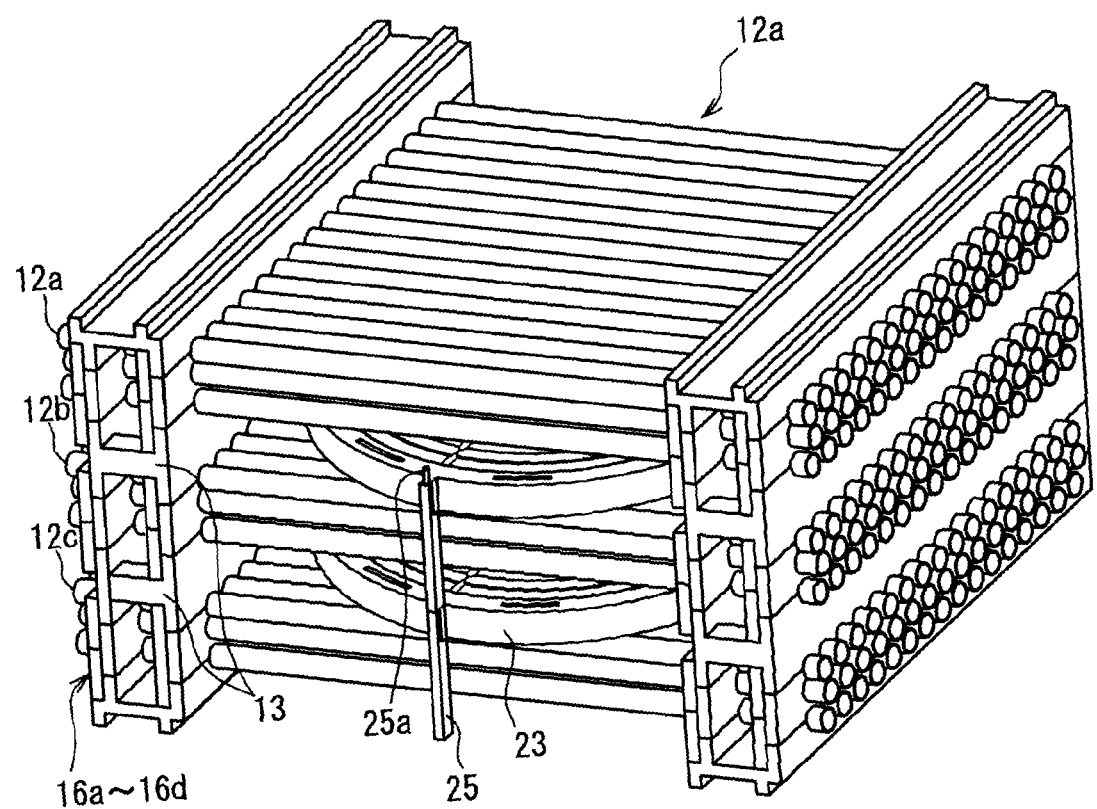
FIG. 13B is a perspective view illustrating the state in which the insertion members are positioned between thin tube bundles.

By inserting the insertion members 20 between the first to third thin tube bundle units 12a-12c and connecting the connecting portions 25 of the upper and lower insertion members 20, the positions of the insertion members 20 with respect to the first to third thin tube bundle units 12a-12c can be held as illustrated in FIG. 13B. The connecting portion 25 has a connecting protrusion 25a at an upper end, and a connecting concave portion (not shown) at a lower end. By fitting the connecting protrusion 25a in the connecting concave portion, the connecting portions 25 can be connected to each other.

As described above, by sealing the first to third thin tube bundle units 12a-12c in combination with the insertion members 20 with the seal members, the insertion members 20 can be fixed while being positioned exactly with respect to the blood channel 5, as illustrated in FIG. 7B.

Figure 14A:
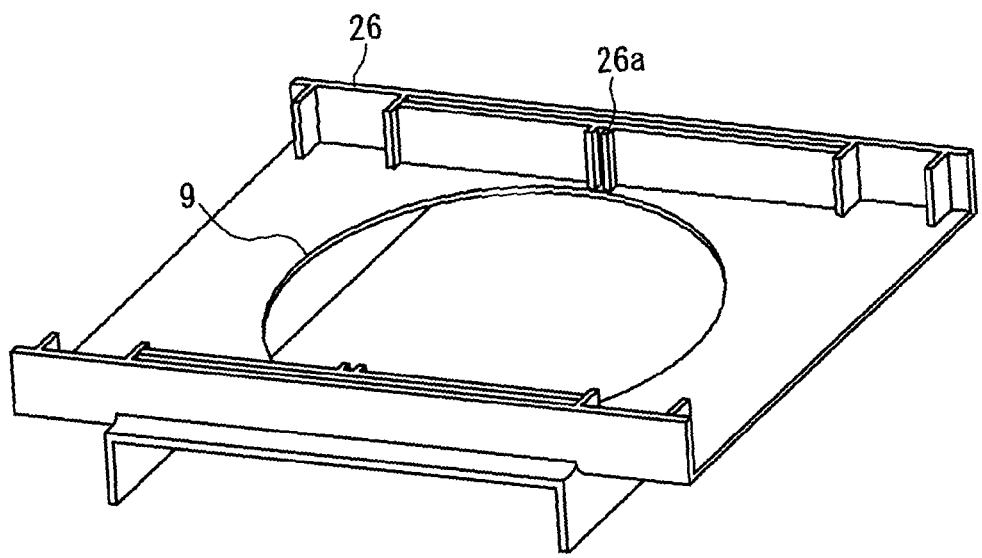
FIG. 14A is a perspective view illustrating a part of a housing having a positioning portion of the insertion member.
Figure 14B:
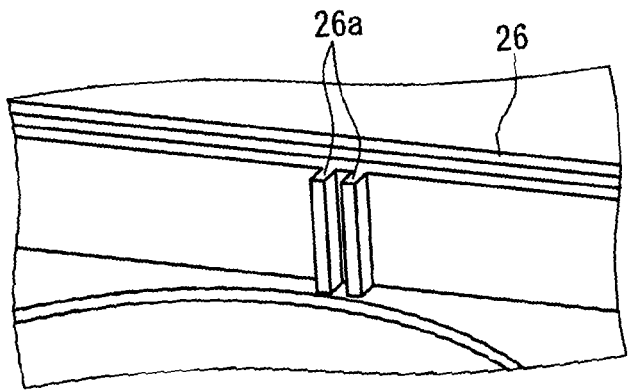
FIG. 14B is an enlarged perspective view of a principal portion illustrating a configuration of the positioning portion of the insertion member.

Another example of the positioning structure of the insertion member 20 will be described with reference to FIGS. 14A-14D. FIG. 14A is a perspective view illustrating a frame 26 that is a part of the housing. A unit in which the first to third thin tube bundle units 12a-12c are combined with the insertion members 20 is mounted in the frame 26, and sealed with the seal members. Positioning ribs 26a are formed on an inner surface of the frame 26. As illustrated in an enlarged state in FIG. 14B, two positioning ribs 26a are provided in parallel.

Figure 14C:
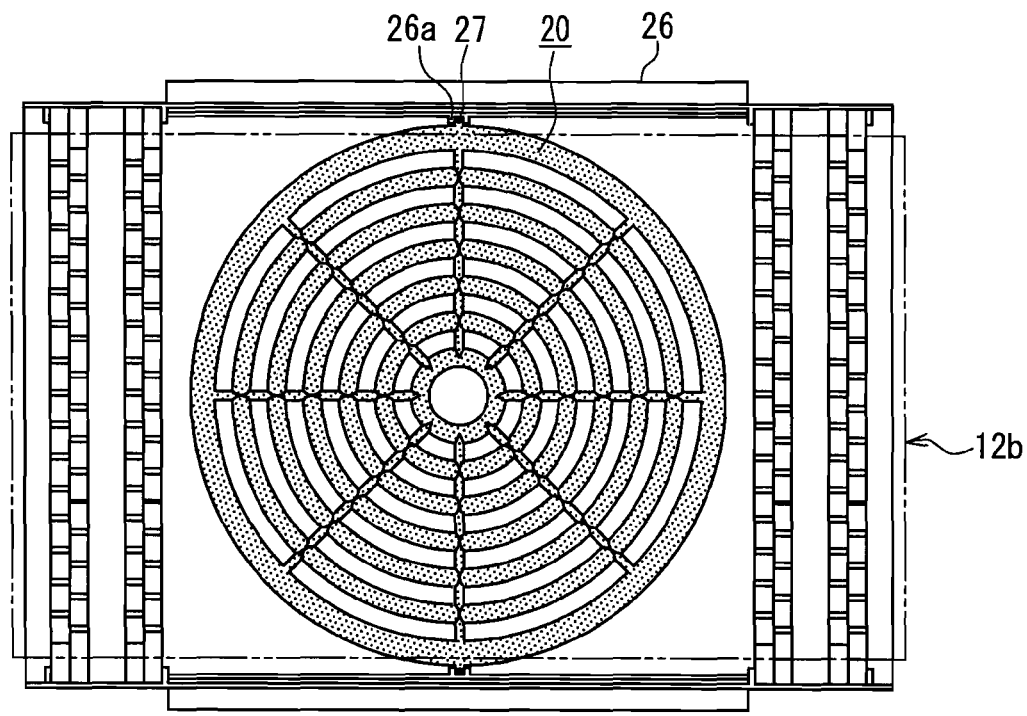
FIG. 14C is a plan view illustrating the state in which the insertion member is positioned by the positioning portion.
Figure 14D:
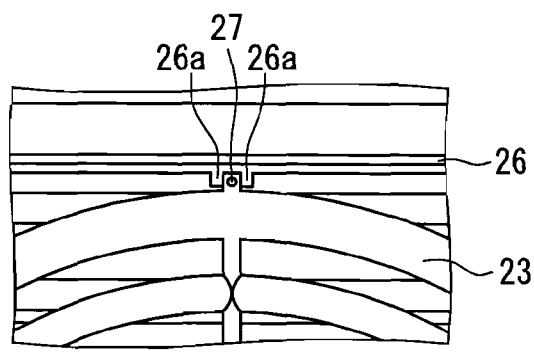
FIG. 14D is a plan view illustrating the principal portion in FIG. 14C in an enlarged state.

FIG. 14C illustrates a state in which the insertion member 20 is positioned by the positioning ribs 26a. In this figure, the first thin tube bundle unit 12a is removed, and regarding the second thin tube bundle unit 12b, the region of the heat transfer thin tubes 1 and the seal members 3a-3c only are indicated by alternate long and two short dashes lines. FIG. 14D illustrates a plan view in which the periphery of the positioning ribs 26a is enlarged. At a circumferential edge of the insertion member 20, a positioning protrusion 27 is formed at a position opposed to the positioning ribs 26a. By engaging the positioning protrusion 27 between the two parallel positioning ribs 26a, the insertion member 20 is positioned with respect to the frame 26. The thin tube bundle unit 12b and the like are positioned with respect to the frame 26, and consequently, the relationships in a planar position between the insertion member 20 and the thin tube bundle unit 12b and the like are determined.

Embodiment 5

Figure 15A:
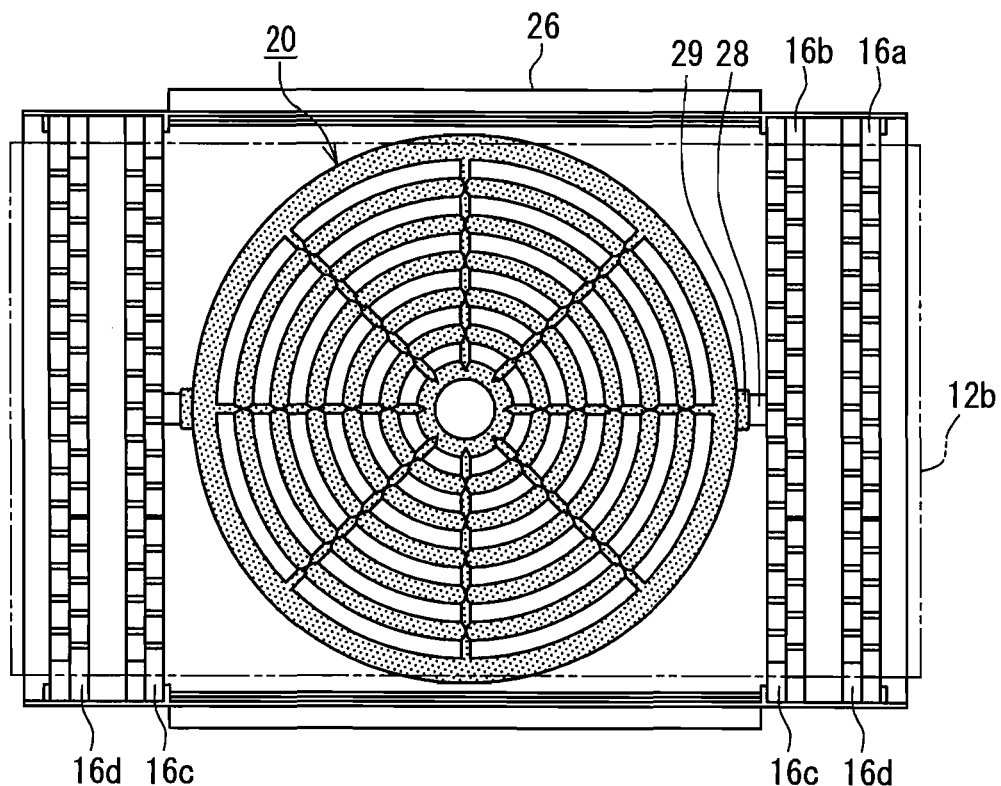
FIG. 15A is a plan view illustrating a method for producing a medical heat exchanger in Embodiment 5.
Figure 15B:
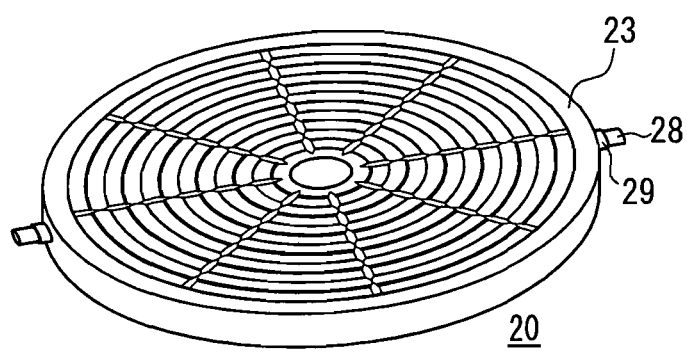
FIG. 15B is a perspective view illustrating a positioning structure of an insertion member used in the production method.

The configuration of a medical heat exchanger in Embodiment 5 and a production method thereof will be described with reference to FIGS. 15A and 15B. FIG. 15A illustrates a state in which the second thin tube bundle unit 12b and the like, and the insertion member 20 are mounted on the frame 26. In the same way as in FIG. 14C, the first thin tube bundle unit 12a is omitted, and the second thin tube bundle unit 12b also is illustrated schematically. The basic structure of the medical heat exchanger produced in the present embodiment is substantially the same as that of the heat exchanger illustrated in FIG. 14O, except for the positioning structure of the insertion members 20.

More specifically, a pair of bridge members 28 are attached to both sides of the insertion member 20, in place of a combination of the positioning ribs 26a and the positioning protrusion 27 in FIG. 14C. As illustrated in FIG. 15B, the bridge members 28 protrude outwardly from the outer circumferential surface of the annular frame 23 of the insertion member 20 in a diameter direction. More specifically, fitting portions 29 having a fitting hole are provided on the outer circumferential surface of the annular frame 23, and one end of the bridge member 28 is fitted in each fitting portion 29 to be held. As illustrated in FIG. 15A, the thin tube bundle unit 12b and the like are mounted on the frame 26 so that a pair of the bridge members 28 of the insertion members 20 are sandwiched between the thin tube row holding members, more exactly, between the thin tube row holding members 16c and the spacers 13. Thus, the insertion members 20 are positioned with respect to the thin tube bundle unit 12b and the like.

As described above, if the insertion members 20 are positioned and mounted between the first to third thin tube bundle units 12a-12c and sealed with the seal members, the insertion members 20 can be fixed while being positioned exactly with respect to the blood channel 5, as illustrated in FIG. 7B. The pressure force caused by the bridge members 28 for holding the insertion member 20 between the thin tube row holding members can be set to be sufficiently large. Thus, the insertion member 20 can be positioned exactly against a large load that acts in a sealing step. Further, it is possible to form a structure in which the thin tube bundle unit 12b and the like are integrated with the insertion members 20 before being mounted on the frame 26, and hence, the sealing operation becomes easy.

What is important here is that the bridge members 28 are made of the same material as that for the seal members 3a-3c. Therefore, after sealing is performed with the seal members 3a-3c, the bridge members 28 are integrated with the seal member 3c. Thus, peeling between the bridge members 28 and the seal member 3c does not occur, and there is no concern that blood may leak in this portion.

As described above, according to the present embodiment, a production method can be realized in which, in the step of sealing with the seal members, the insertion members are positioned exactly with respect to the thin tube bundle units, and further, the leakage of blood caused by the positioning structure does not occur after sealing.

Embodiment 6

Figure 16B:
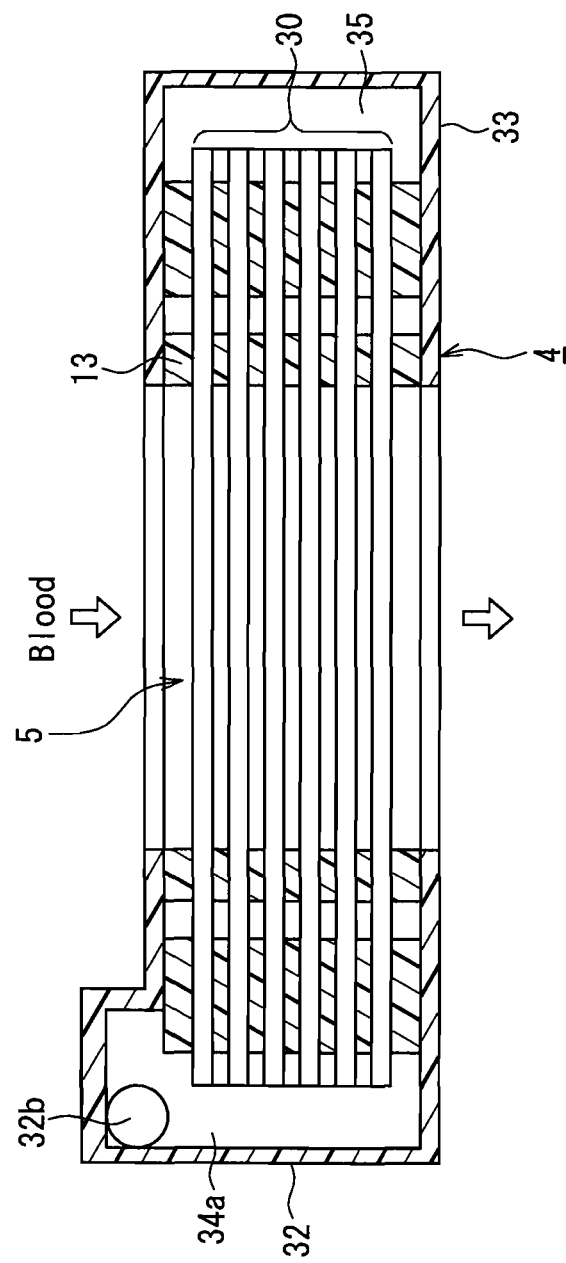
FIG. 16B is a cross-sectional view taken along the line E-E of the medical heat exchanger.

FIG. 16A is a plan view illustrating a heat exchanger in Embodiment 6. FIG. 16B is a cross-sectional view taken along the line E-E of FIG. 16A. The elements similar to those illustrated in FIG. 1A and the like of Embodiment 1 are denoted with the reference numerals similar to those therein, and the repeated descriptions thereof will be omitted.

In the present embodiment, a thin tube bundle 30 has a horizontal turnback structure divided in a transverse direction with respect to the flow direction of the blood channel 5 that is a heat exchange channel, i.e., in a planar direction in the plan view of FIG. 16A. Two groups of thin tube bundle units 31a, 31b are formed and arranged horizontally. A predetermined interval is provided between the thin tube bundle units 31a, 31b with a spacer (not shown).

The housing 4 has a cool/warm water inlet/outlet header 32 and a cool/warm water reflux header 33. In the cool/warm water inlet/outlet header 32, a flow chamber is partitioned into an inlet chamber 34a and a outlet chamber 34b with a partition wall 32a. In the inlet chamber 34a, one of ends of the thin tube bundle unit 31a is placed, and in the outlet chamber 34b, one of ends of the thin tube bundle unit 31b is placed. Further, the cool/warm water inlet/outlet header 32 has a cool/warm water inlet port 32b communicating with the inlet chamber 34a and a cool/warm water outlet port 32c communicating with the outlet chamber 34b. In the cool/warm water reflux header 33, a flow chamber is not divided, and an integral reflux chamber 35 is formed. In the reflux chamber 35, the other of the ends of the thin tube bundle units 31a, 31b are placed.

Cool/warm water introduced from the cool/warm water inlet port 32b to the inlet chamber 34a flows through lumens of the heat transfer thin tubes 1 of the thin tube bundle unit 31a and flows in the reflux chamber 35 of the cool/warm water reflux header 33. Further, the cool/warm water enters the heat transfer thin tubes 1 of the thin tube bundle unit 31b and flows therethrough to reach the outlet chamber 34b, and flows out of the cool/warm water outlet port 32c.

Accordingly, the cool/warm water to be introduced is allowed to pass through one half of the thin tube bundle 30 to the other half thereof successively by the cool/warm water inlet/outlet header 32 and the cool/warm water reflux header 33. Thus, the form of a divided flow can be obtained, in which the cool/warm water to be introduced passes through a plurality of groups of divided thin tube bundle units successively in the same way as in Embodiment 1. Compared with the simultaneous flow, the flow speed of the cool/warm water flowing through the heat transfer thin tubes 1 can be increased and the film resistance in an inner wall of the heat transfer thin tubes 1 can be reduced, and hence, heat exchange efficiency can be enhanced.

Embodiment 7

Figure 17A:
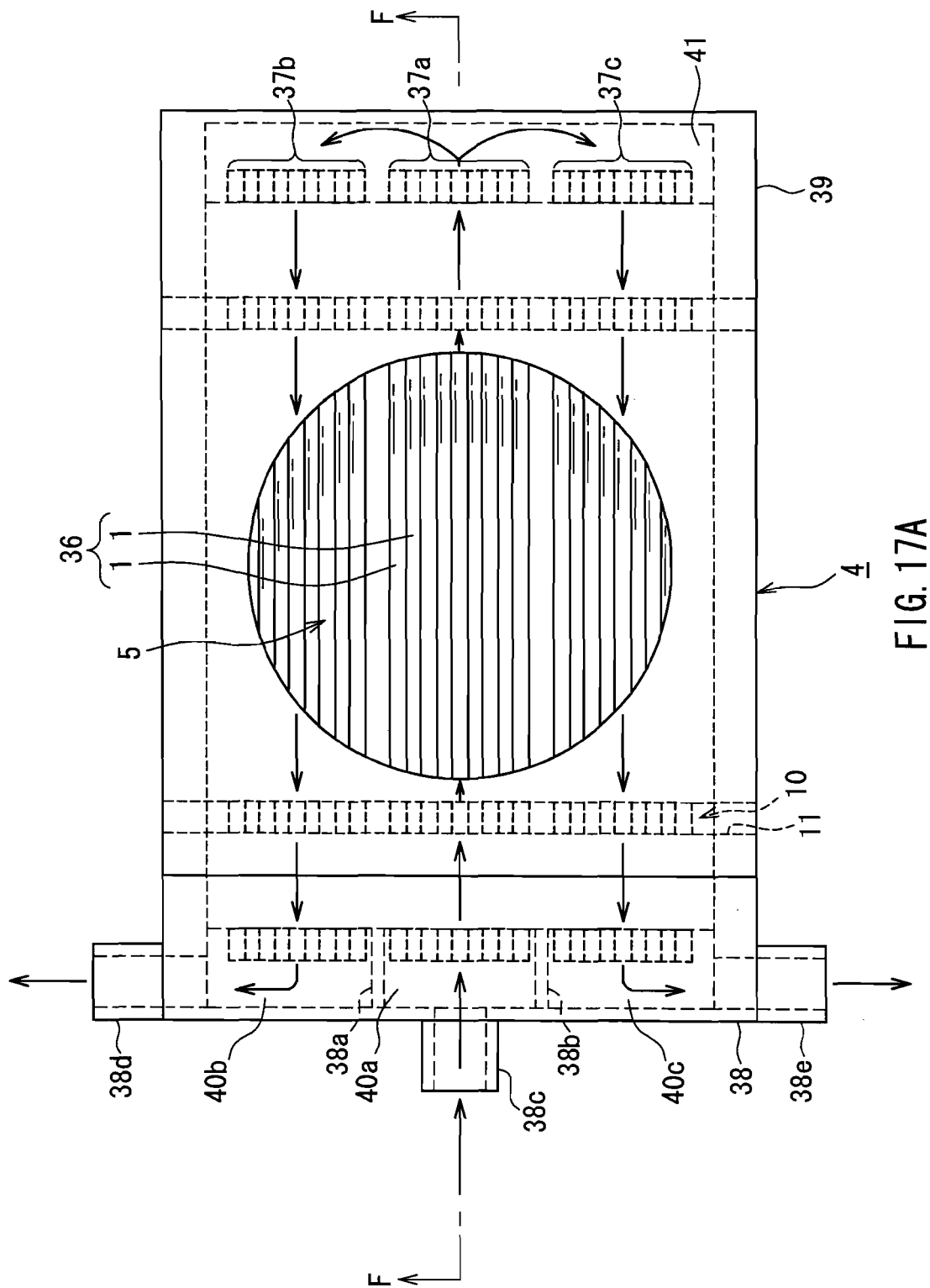
FIG. 17A is a top view illustrating a configuration of a medical heat exchanger in Embodiment 7.
Figure 17B:
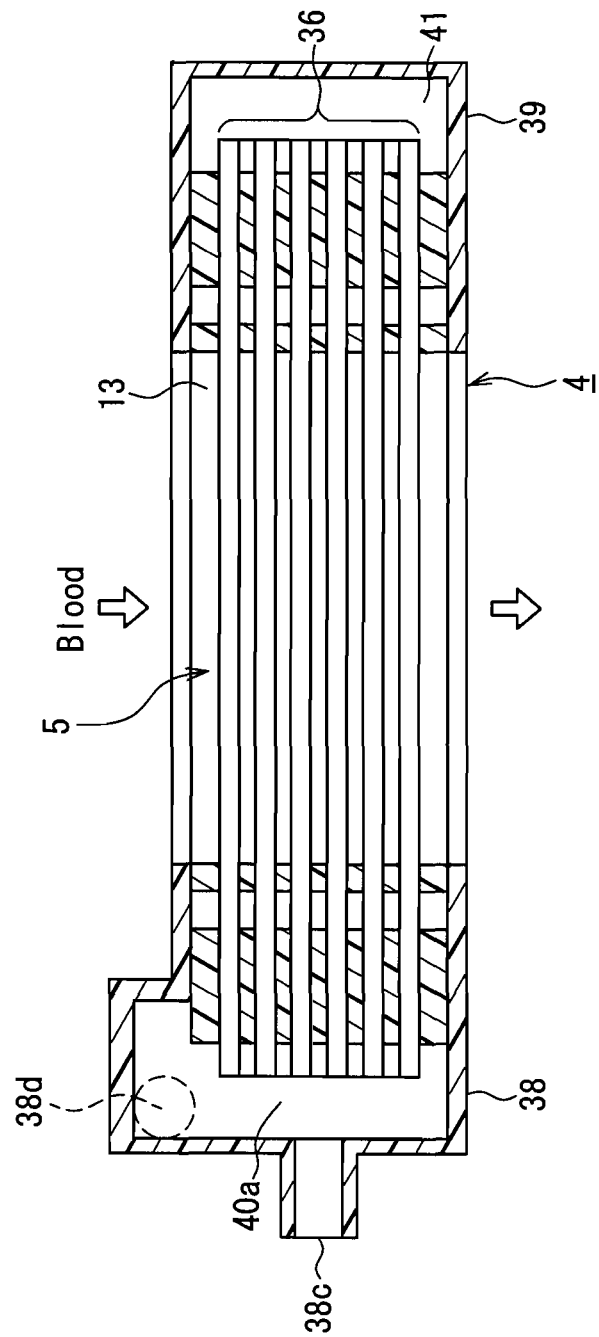
FIG. 17B is a cross-sectional view taken along the line F-F of the medical heat exchanger.

FIG. 17A is a plan view illustrating a heat exchanger in Embodiment 7. FIG. 17B is a cross-sectional view taken along the line F-F of FIG. 17A. The elements similar to those illustrated in FIGS. 16A and 16B of Embodiment 6 are denoted with the same reference numerals as those therein, and the repeated descriptions thereof will be omitted.

Also in the present embodiment, a thin tube bundle 36 has a horizontal turnback structure in the same way as in Embodiment 6. However, in the present embodiment, the thin tube bundle 36 is divided into three to form a center thin tube bundle unit 37a, and side thin tube bundle units 37b, 37c positioned on both sides of the center thin tube bundle unit 37a, which are arranged horizontally. Predetermined intervals are provided between the center thin tube bundle unit 37a and each of the side thin tube bundle units 37b, 37c with spacers (not shown).

The housing 4 has a cool/warm water inlet/outlet header 38 and a cool/warm water reflux header 39. In the cool/warm water inlet/outlet header 38, a flow chamber is partitioned into an inlet chamber 40a at the center and outlet chambers 40b, 40c at both sides thereof with partition walls 38a, 38b. In the inlet chamber 40a, the end of the center thin tube bundle unit 37a is placed. In the outlet chambers 40b, 40c, the ends of the side thin tube bundle units 37b, 37c respectively are placed. Further, the cool/warm inlet/outlet header 38 has a cool/warm water inlet port 38c communicating with the inlet chamber 40a and cool/warm water outlet ports 38d, 38e communicating with the outlet chambers 40b, 40c. The flow chamber in the cool/warm water reflux header 39 is not divided, and an integral reflux chamber 41 is formed. In the reflux chamber 41, the end of the center thin tube bundle unit 37a and the respective ends of the side thin tube bundle units 37b, 37c are placed.

The cool/warm water introduced from the cool/warm water inlet port 38c to the inlet chamber 40a flows through lumens of the heat transfer thin tubes 1 of the center thin tube bundle unit 37a and flows in the reflux chamber 41 of the cool/warm water reflux header 39. Further, the cool/warm water enters the heat transfer thin tubes 1 of the side thin tube bundle units 37b, 37c and flows therethrough to reach the inlet chambers 40b, 40c, and flows out of the cool/warm water outlet ports 38d, 38e.

Thus, the cool/warm water to be introduced is allowed to pass from the center portion of the thin tube bundle 36 to both sides thereof successively by the cool/warm water inlet/outlet header 38 and the cool/warm water reflux header 39. Thus, the function of the divided flow is obtained in which the cool/warm water to be introduced passes through a plurality of groups of divided thin tube bundle units in the same way as in Embodiment 1. This can increase the flow speed of the cool/warm water flowing through the heat transfer thin tubes 1, compared with the simultaneous flow, and the film resistance in the inner wall of the heat transfer thin tubes 1 can be reduced and the heat exchange efficiency can be enhanced.

Figure 18:
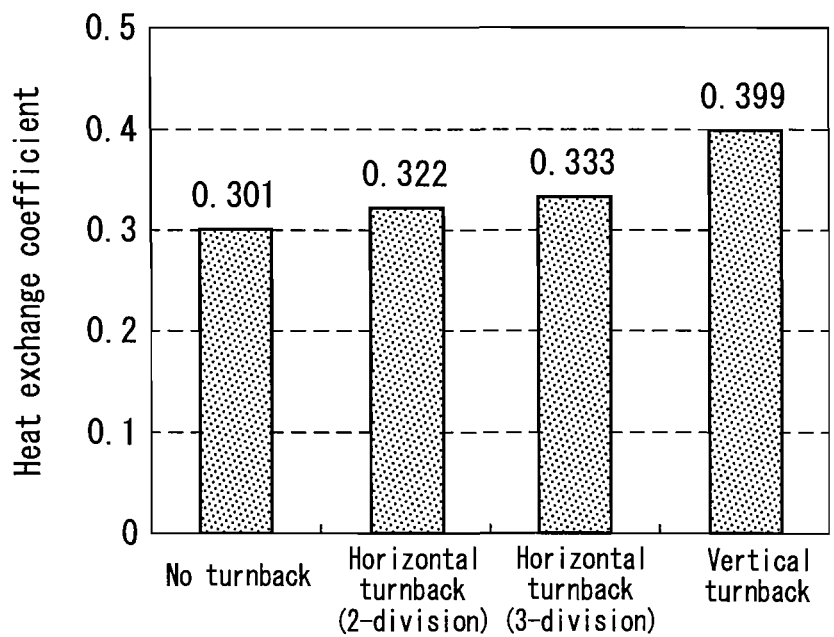
FIG. 18 is a diagram illustrating a relationship between the turnback structure of the heat exchanger and the heat exchange coefficient in Embodiments 6 and 7.

FIG. 18 illustrates the results of the comparison of the heat exchange coefficient of the heat exchangers having the configurations shown in Embodiments 1 to 3 with the heat exchange coefficient having a configuration of a simultaneous flow (no turnback) in the conventional example. The horizontal turnback (two-way division) corresponds to the configuration shown in Embodiment 6, the horizontal turnback (three-way division) corresponds to the configuration shown in Embodiment 7, and the vertical turnback corresponds to the configuration shown in Embodiment 1. In any case, the opening diameter of the blood channel 5 was set at 70 mm and the number of layers of the heat transfer thin tubes 1 was set at 12.

As illustrated in FIG. 18, in the case of the horizontal turnback (two-way division), the horizontal turnback (three-way division), and the vertical turnback, the heat exchange coefficient was enhanced by 7%, 11%, and 33% respectively, compared with the case of no turnback. Thus, it is apparent that the heat exchange efficiency is enhanced by the divided flow. Further, in the case of the horizontal turnback (three-way division), the heat exchange efficiency is enhanced compared with the horizontal turnback (two-way division). This is because the heat exchange area is larger in the center portion of the thin tube bundle 36 compared with that in the side portions due to the circular cross-section of the blood channel 5, and the film area contributing to heat exchange is large. More specifically, it is considered that the cool/warm water at a high temperature flows through a region with a large heat exchange area by allowing the cool/warm water to flow first from the center portion, which contributes to the enhancement of heat exchange efficiency. Further, in the case of the vertical turnback, the heat exchange efficiency is enhanced by allowing cool/warm water to flow in a counterflow, compared with the horizontal turnback (three-way division).

Embodiment 8

Figure 19:
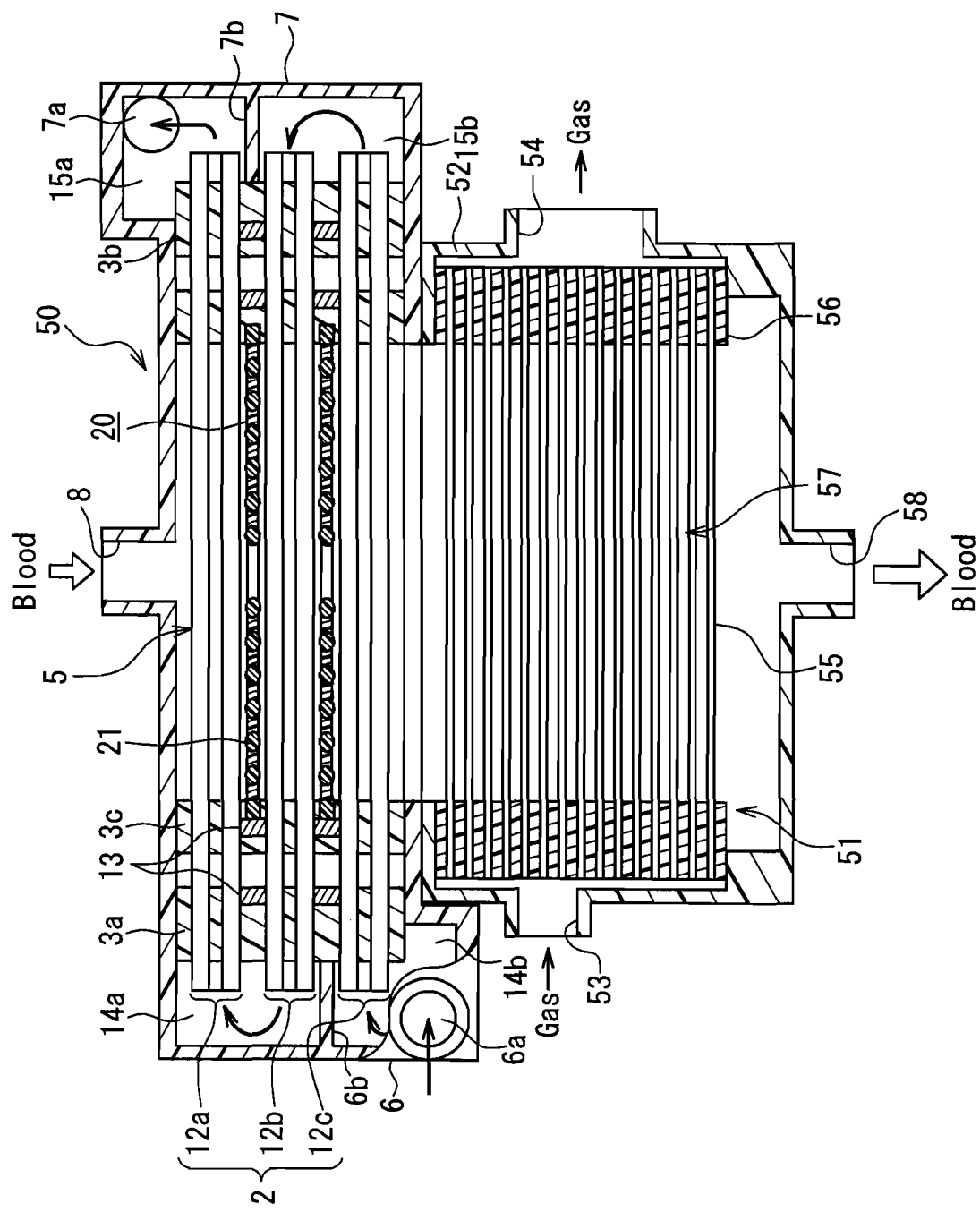
FIG. 19 is a cross-sectional view illustrating an artificial lung device in Embodiment 8.
Figure 20A:
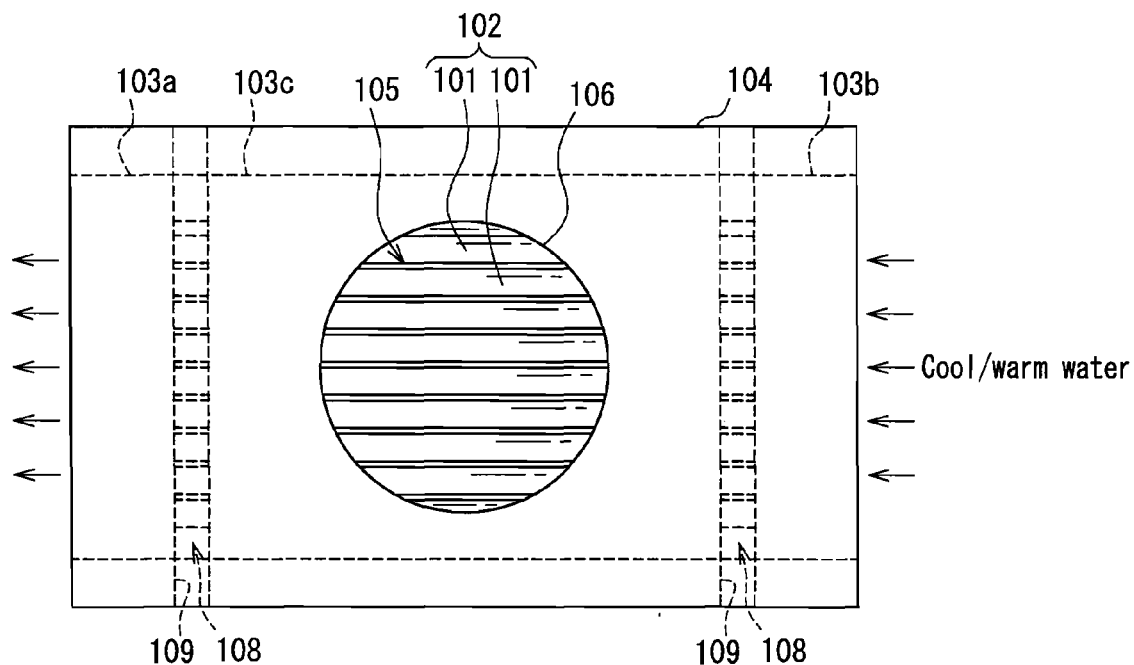
FIG. 20A is a top view illustrating a configuration of a heat exchanger in a conventional example.
Figure 20B:
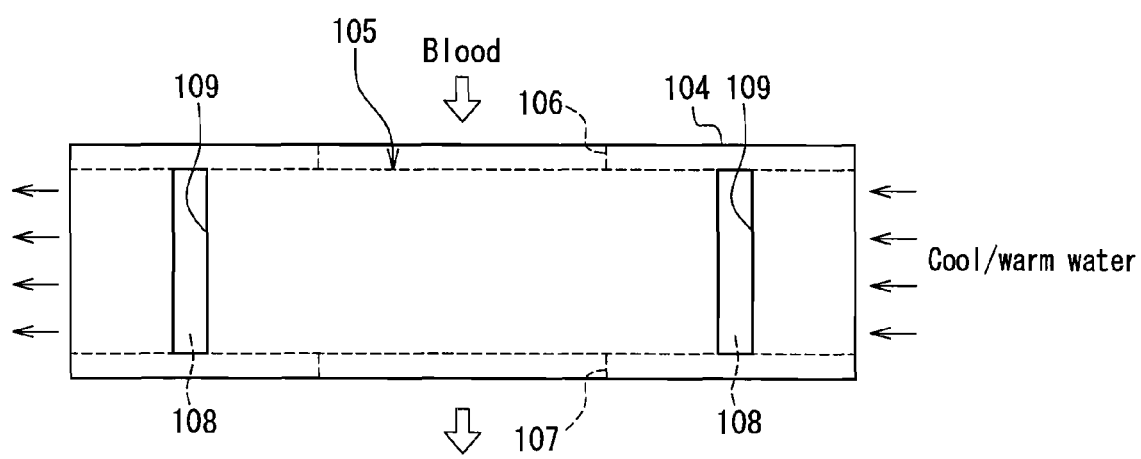
FIG. 20B is a side view illustrating the configuration of the same heat exchanger.
Figure 20C:
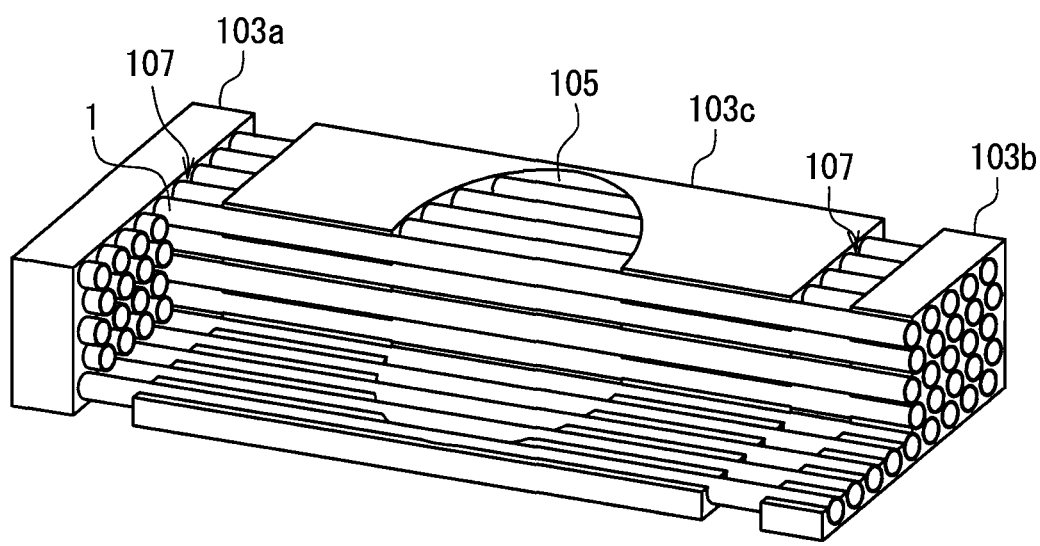
FIG. 20C is a perspective view illustrating a partial cross-section of an inside of a housing in the same heat exchanger.

FIG. 19 is a cross-sectional view illustrating an artificial lung device in Embodiment 8. The artificial lung device has a configuration in which a heat exchanger 50 in Embodiment 3 is combined with an artificial lung 51. It should be noted that the artificial lung device also can have a configuration in which any of the heat exchangers in the above-mentioned other embodiments is provided instead of the heat exchanger 50.

The heat exchanger 50 is stacked on the artificial lung 51, and the housing 4 of the heat exchanger 50 is connected to a housing 52 of the artificial lung 51. It should be noted that the housing 4 of the heat exchanger 50 also may be integrated with the housing 52 of the artificial lung 51. In the region of the artificial lung 51, a gas inlet path 53 for introducing oxygen gas and a gas outlet path 54 for discharging carbon dioxide or the like in blood are provided.

The artificial lung 51 includes a plurality of hollow fiber membranes 55 and seal members 56. The seal members 56 seal the hollow fiber membranes 55 so that blood does not enter the gas inlet path 53 and the gas outlet path 54. The seal members 56 seal the hollow fiber membranes 55 in such a manner that both ends of the hollow fibers constituting the hollow fiber membranes 55 are exposed. The gas inlet path 53 and the gas outlet path 54 communicate with each other through the hollow fibers constituting the hollow fiber membranes 55.

Further, the space in which the seal members 56 are not present in the artificial lung 51 constitutes a blood channel 57 in a cylindrical shape, and the hollow fiber membranes 55 are exposed in the blood channel 57. Further, a blood inlet side of the blood channel 57 communicates with an outlet side of the blood channel 5 of the heat exchanger 50.

With the above-mentioned configuration, the blood introduced from the blood inlet port 8 and is subjected to heat exchange through the blood channel 5 flows in the blood channel 57 and comes into contact with the hollow fiber membranes 55. At this time, oxygen gas flowing through the hollow fiber membranes 55 is taken in the blood. Further, the blood with oxygen gas taken therein is discharged outside through the blood outlet port 58 provided at the housing 52 and returned to a patient. On the other hand, carbon dioxide in the blood is taken in the hollow fiber membranes 55, and thereafter, is discharged through the gas outlet path 54.

Thus, in the artificial lung device illustrated in FIG. 19, the temperature of the blood is adjusted by the heat exchanger 50, and the blood with the temperature adjusted is subjected to gas exchange by the artificial lung 51. Further, at this time, even if seal leakage occurs in the heat exchanger 50, and the cool/warm water flowing through the heat transfer thin tubes 1 flows out, the cool/warm water appears in the gaps 10, and hence, the leakage can be detected. Therefore, the artificial lung device illustrated in FIG. 19 can detect seal leakage, and the contamination of blood by the cool/warm water can be suppressed.

INDUSTRIAL APPLICABILITY

According to the present invention, since the flow speed of the cool/warm water flowing through heat transfer thin tubes can be increased, the heat exchange efficiency can be enhanced while the film resistance in the inner wall of the heat transfer thin tubes is reduced to suppress the increase in volume in the heat exchange region. Thus, the present invention is useful as a medical heat exchanger used in an artificial lung device or the like.

The invention claimed is:

1. A medical heat exchanger, comprising:
a thin tube bundle in which a plurality of heat transfer thin tubes for letting heat medium liquid flow through a lumen are arranged and stacked;
a seal member sealing the thin tube bundle while allowing both ends of the heat transfer thin tubes to be exposed and forming a blood channel that allows blood to flow therethrough so that the blood comes into contact with each outer surface of the heat transfer thin tubes;
a housing containing the seal member and the thin tube bundle and provided with a blood inlet port and a blood outlet port positioned respectively at both ends of the blood channel;
a pair of heat transfer thin tube headers provided at respective side ends of the thin tube bundle so as to form a pair of flow chambers that surround the respective ends of the thin tube bundle; and
a liquid inlet port and a liquid outlet port of the heat medium liquid provided at one of the headers or the respective headers,
wherein the thin tube bundle is divided in a flow direction of the blood channel into a plurality of thin tube bundle units each including a plurality of the heat transfer thin tubes, forming a stack structure of a plurality of stages of the thin tube bundle units,
spacers are mounted between each of the plurality of stages of thin tube bundle units to form gaps of a predetermined interval between the respective stages,
in a region inside the blood channel, an insertion member is paced in each of the gaps so as to fill a part of a volume of the gap, and the insertion member has a channel communicating with the blood channel,
at least one of the flow chambers is partitioned into a plurality of flow compartments by a partition wall positioned at a boundary between the thin tube bundle units, and
the heat transfer thin tube headers are configured so that the heat medium liquid to be introduced passes through the plurality of thin tube bundle units successively via each of the flow compartments; wherein the partition wall is positioned so as to correspond to each of the gaps thereby forming a channel such that the heat medium liquid flowing in from the liquid inlet port passes through the plurality of stages of thin tube bundle units successively via any one of the flow compartments and flows out of the liquid outlet port via any other of the flow compartments.

2. The medical heat exchanger according to claim 1, wherein the heat transfer thin tube headers are formed so that the heat medium liquid successively passes from the thin tube bundle unit in a lower stage placed on a downstream side of the blood channel to the thin tube bundle unit in an upstream stage placed on an upstream side.

3. The medical heat exchanger according to claim 1, wherein the thin tube bundle is divided into three stages of the thin tube bundle units.

4. The medical heat exchanger according to claim 3, wherein a total number of the heat transfer thin tubes constituting the thin tube bundle unit in each stage is two or three layers.

5. The medical heat exchanger according to claim 1, wherein the blood channel is formed in a cylindrical shape whose circumference is sealed with the seal member.

6. The medical heat exchanger according to claim 1, wherein a pair of the spacers are placed respectively in regions sealed with the seal member on both sides of the blood channel.

7. The medical heat exchanger according to claim 6, wherein the pair of the spacers are coupled with each other to be integrated.

8. The medical heat exchanger according to claim 1, wherein the thin tube bundle units include thin tube row holding members holding an arrangement state of the plurality of the heat transfer thin tubes, and
the spacers are mounted between the thin tube row holding members opposed to each other between the stages of the adjacent thin tube bundle units.

9. The medical heat exchanger according to claim 1, wherein
the flow chamber is partitioned into the flow compartments corresponding to a pair of single stages of the thin tube bundle unit positioned at an upstream end and a downstream end of the blood channel and the flow compartments corresponding to respective other pairs of stages of the thin tube bundle units, and
the liquid inlet port and the liquid outlet port are provided at the respective positions of the header/headers facing the flow compartments corresponding to the single stages of the thin tube bundle unit.

10. The medical heat exchanger according to claim 9, wherein the thin tube bundle units are formed in three stages,
one of the heat transfer thin tube headers includes the flow compartment corresponding to the one stage of the thin tube bundle unit positioned at the upstream end of the blood channel and the flow compartment corresponding to the two stages of the thin tube bundle units on a downstream side,
the other heat transfer thin tube header includes the flow compartment corresponding to the one stage of the thin tube bundle unit positioned at the downstream end of the blood channel and the flow compartment corresponding to the two stages of the thin tube bundle units on an upstream side, and
the liquid inlet port is provided in the flow compartment corresponding to the thin tube bundle unit at the downstream end and the liquid outlet port is provided in the flow compartment corresponding to the thin tube bundle unit at the upstream end.

11. The medical heat exchanger according to claim 1, wherein the insertion member includes a plurality of annular ribs arranged concentrically and connection ribs extending radially in a diameter direction of the annular ribs and connecting the respective annular ribs.

12. The medical heat exchanger according to claim 11, wherein the annular rib has an oval cross-sectional shape with a direction of the blood channel being a minor axis.

13. The medical heat exchanger according to claim 1, wherein a pair of the spacers are placed respectively in the sealed regions on both sides of the blood channel, and
the spacers and the insertion members are made of materials different from each other.

14. The medical heat exchanger according to claim 13, comprising a connecting portion connecting a plurality of the insertion members placed between the respective stages of the thin tube bundle units at a side edge of the thin tube bundle.

15. The medical heat exchanger according to claim 13, comprising a positioning member placed at a side edge of the thin tube bundle, and
each of the plurality of the insertion members placed between the respective stages of the thin tube bundle units has an engagement portion that is engaged with the positioning member in a part of a circumferential edge, and is positioned with respect to the thin tube bundle by the engagement.

16. The medical heat exchanger according to claim 15, wherein the positioning member is formed on an inner wall of the housing.

17. The medical heat exchanger according to claim 13, wherein an arrangement state of the heat transfer thin tubes in the thin tube bundle unit is held by thin tube row holding members placed at both ends of the thin tube bundle,
the spacers are mounted between the thin tube row holding members opposed to each other between the adjacent stages of the thin tube bundle,
a pair of bridge members further are provided, which are made of the same material as that of the seal member and placed between a pair of the thin tube row holding members and the insertion member, and
the bridge members abut against the insertion member and the pair of the thin tube row holding members and are sealed in the seal member.

18. A method for producing the medical heat exchanger as defined in claim 1, comprising:
a thin tube bundle unit formation step of forming the thin tube bundle units, using a thin tube row holding member holding an arrangement state of the heat transfer thin tubes;
a thin tube bundle module formation step of forming a thin tube bundle module by stacking a plurality of the thin tube bundle units while placing spacers at both ends between respective stages and interposing an insertion member that fills a part of a gap between the thin tube bundle units between the respective stages in a center portion of the thin tube bundle units; and
a sealing step of sealing the thin tube bundle module with the seal member so that the blood channel is formed in a region including the insertion member, with the insertion member having a channel communicating with the blood channel, while exposing both ends of the thin tube bundle,
wherein in the thin tube bundle module formation step, bridge members made of the same material as that of the seal member are placed between a pair of the thin tube row holding members and the insertion member so as to abut against the pair of the thin tube row holding members and the insertion member respectively, whereby the insertion member is held between the thin tube row holding members, and
in the sealing step, the bridge members are sealed in the seal member.

19. An artificial lung device, comprising:
the heat exchanger according to claim 1; and
an artificial lung having a blood channel that crosses a gas channel so as to perform gas exchange,
wherein the heat exchanger and the artificial lung are stacked, and the blood channel of the heat exchanger and the blood channel of the artificial lung communicate with each other.

* * * * *